United States Patent
Hofler et al.

(10) Patent No.: US 6,723,320 B2
(45) Date of Patent: Apr. 20, 2004

(54) MUTATIONS OF E CADHERIN AS A BASIS FOR THE DIAGNOSIS AND THERAPY OF HUMAN MALIGNANT TUMORS

(75) Inventors: Heinz Hofler, Munich (DE); Karl-Friedrich Becker, Garching bei Munchen (DE); Elizabeth Kremmer, Freising (DE); Manfred Eulitz, Munich (DE); Christoph Schuhmacher, Munich (DE)

(73) Assignee: GSF Forschungszentrum fur Umwelt und Geshundheit GmbH, Oberschleissheim (DE)

(*) Notice: Subject to any disclaimer, the term of this patent is extended or adjusted under 35 U.S.C. 154(b) by 99 days.

(21) Appl. No.: 10/047,403

(22) Filed: Jan. 14, 2002

(65) Prior Publication Data
US 2003/0054005 A1 Mar. 20, 2003

Related U.S. Application Data

(63) Continuation-in-part of application No. 08/899,279, filed on Jul. 23, 1997, now Pat. No. 6,447,776.

(30) Foreign Application Priority Data

Jul. 24, 1999 (DE) .......................................... 196 29 938

(51) Int. Cl.[7] .......................... A61K 41/00; G01N 33/53; C12P 21/08
(52) U.S. Cl. .................. 424/181.1; 435/7.1; 530/391.1; 530/391.7
(58) Field of Search ........................... 424/138.1, 178.1, 424/181.1; 530/388.23, 391.3, 391.7; 435/7.1, 326

(56) References Cited

U.S. PATENT DOCUMENTS 6,447,776 B1 * 9/2002 Hofler et al.

FOREIGN PATENT DOCUMENTS

| DE | 41 10 405 A1 | 10/1992 |
|---|---|---|
| JP | 7-500723 | 1/1995 |
| WO | WO 94/11401 A1 | 5/1994 |

OTHER PUBLICATIONS

Dillman RO. Antibodies as cytotoxic therapy. J Clin Oncol. 1994 Jul;12(7):1497–515.*
Becker, K–F. et al., "Exon Skipping in the E–cadherin Gene Transcript in Metastatic Human Gastric Carcinomas," *Human Molecular Genetics* (1993) 2(6): 803–804.
Becker, K–F. et al., "Frequent Somatic Allelic Inactivation of the E–cadherin Gene in Gastric Carcinomas," *Journal of the National Cancer Institute* (Jul. 19, 1995) 87(14): 1082–1084.
Becker, K–F. et al., "Single Nucleotide Polymorphisms in the Human E–cadherin Gene," *Hum. Gener.* (1995) 96: 739–740.
Becker, K–F. et al., "E–Cadherin Gene Mutations Provide Clues to Diffuse Type Gastric Carcinomas," *Cancer Research* (Jul. 15, 1994) 54: 3845–3852.
Senekowitsch–Schmidtke et al., "Highly Specific Tumor Binding of a $^{213}$Bi–labeled Monoclonal Antibody Against Mutant E–Cadherin Suggests Its Usefulness for Locoregional ∝–Radioimmunotherapy of Diffuse–Type Gastric Cancer," Cancer Research, 61:2804–2808, 2001.
Becker, K.F. et al., "Analysis of E–cadherin in diffuse–type gastric cancer using a mutation–specific monoclonal antibody," American Journal of Pathology, Dec. 1999, pp. 1803–1809, vol. 155.
Becker, K.F. and Hofler, H., "Frequent somatic allelic inactivation of the E–cadherin gene in gastric carcinomas," Journal of the National Cancer Institute, Jul. 1995, pp. 1082–1084, vol. 87(14).
Becker, K.F. and Reich, U., "Single nucleotide polymorphisms in the human E–cadherin gene," Hum. Genet., 1995, pp. 739–740, vol. 96.
Becker, K.F. et al., "E–cadherin gene mutations provide clues to diffuse type gastric carcinomas," Cancer Research, Jul. 1994, pp. 3845–3852, vol. 54.
Becker, K.F., et al., "Exon skipping in the E–cadherin gene transcript in metastatic human gastric carcinomas," Human Molecular Genetics, 1993, pp. 803–804, vol. 2(6).
Bringuier, P.P. et al., "Decreased E–cadherin immunoreactivity correlates with poor survival in patients with bladder tumors," Cancer Research, Jul. 1993, pp. 3241–3245, vol. 53.
Hofler, H. and Becker, K.F., "Gastric carcinogenesis: New strategies of diagnosis and therapy on the basis of molecular biology," Monduzzi Editore, 1997, pp. 393–398, Bologna, Italien.
Hofler, H. et al., "Gastric carcinogenesis: New strategies of diagnosis and therapy on the basis of molecular biology," Monduzzi Editore, 1996, pp. 93–97, Bologna, Italien.
Oda, T. et al., "E–Cadherin gene mutations in human gastric carcinoma cell lines," Proc. Natl. Acad. Sci. USA, Mar. 1994, pp. 1858–1862, vol. 91.
Schuhmacher, C. et al., "E–cadherin mutation specific antibody in gastric cancer: proposal for a multi–center study to open novel clinical avenues," Monduzzi Editore, 1997, pp. 427–431, Bologna, Italien.

* cited by examiner

Primary Examiner—Christina Chan
Assistant Examiner—Maher Haddad
(74) Attorney, Agent, or Firm—Townsend and Townsend and Crew LLP

(57) ABSTRACT

The present invention describes monoclonal antibodies which are useful for the specific detection and therapy of diffuse gastric carcinoma. Further embodiments describe therapeutic and diagnostic means for the detection and for the therapy of diffuse gastric carcinomas as well as methods for the detection and therapy of diffuse gastric carcinomas.

8 Claims, 9 Drawing Sheets

Immunofluorescence. Mutated E-cadherin protein (exon 9 deletion) can be detected at the cellular junctions (bright lines) of transfected cells (see text)

Immunoelectron microscopy. Mutated E-cadherin protein (arrows) can be detected at the membrane of transfected cells (see text)

Rapid diagnosis of E-cadherin.

Western blot using mutation specific E-cadherin antibody 7E6. In contrast to the not mutation-specific E-cadherin antibody HECD-1, the mutation-specific antibody 7E6 exclusively detects mutated E-cadherin protein. del9, exon 9 deleted E-cadherin; WT, wild-type; -, untransfected.

Immunohistochemistry using mutation-specific E-cadherin antibody 7E6. The mutation-specific antibody 7E6 exclusively detects tumour cells (arrows) of a diffuse-type gastric carcinoma. Non-tumourous glands (arrowheads) are not labeled.

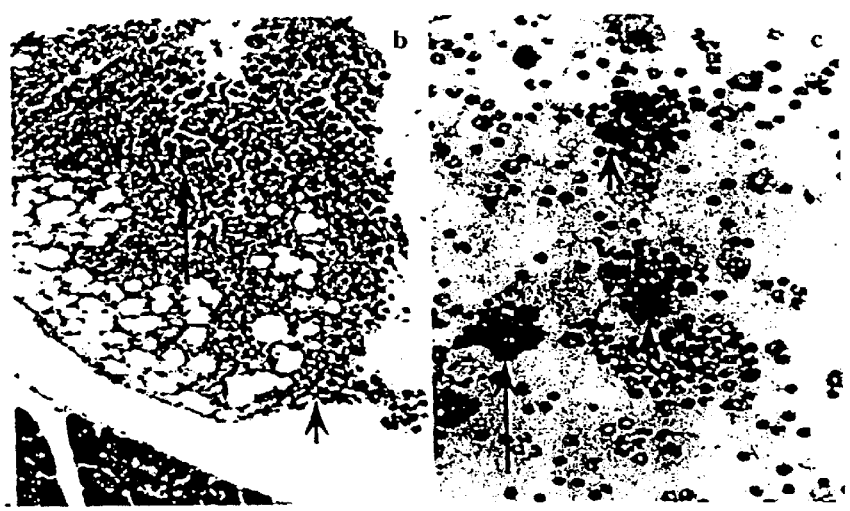
FIGS. 7A-C

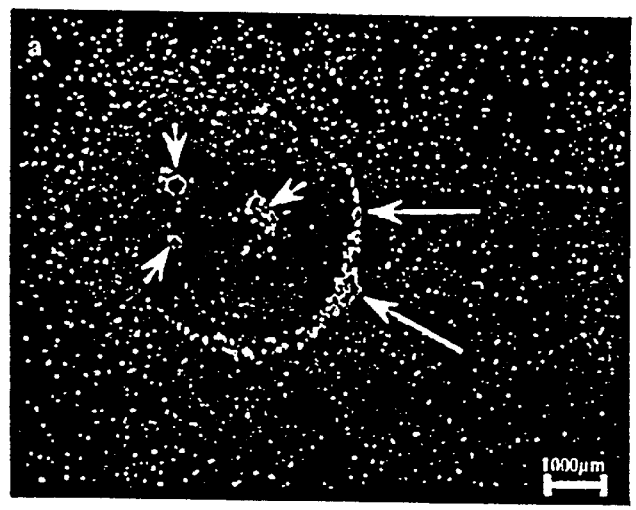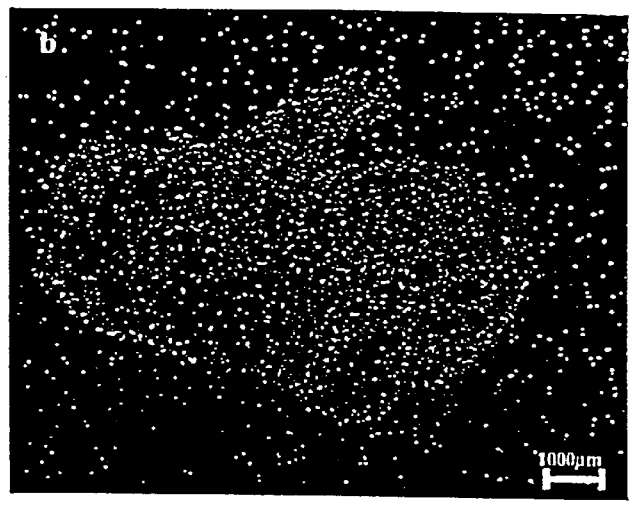
FIGS. 8A-B

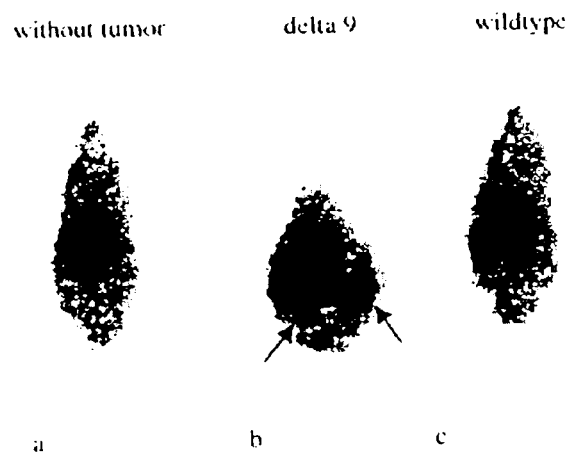
FIGS. 9A-C

SEQUENCE LISTING (1) GENERAL INFORMATION:

(iii) NUMBER OF SEQUENCES: 48

(2) INFORMATION FOR SEQ ID NO: 1:

(i) SEQUENCE CHARACTERISTICS:
      (A) LENGTH: 20 amino acids
      (B) TYPE: amino acid
      (C) STRANDEDNESS: <Unknown>
      (D) TOPOLOGY: linear (ii) MOLECULE TYPE: peptide (ix) FEATURE:
      (A) NAME/KEY: Peptide
      (B) LOCATION: 1..20
      (D) OTHER INFORMATION: /note= "amino acid sequence translated from nucleotides at positions 534 through 593 in "normal" human E-cadherin cDNA"

(xi) SEQUENCE DESCRIPTION: SEQ ID NO: 1:

Pro Gly Leu Arg Arg Gln Lys Arg Asp Trp Val Ile Pro Pro Ile Ser
1               5                   10                  15

Cys Pro Glu Asn
            20

(2) INFORMATION FOR SEQ ID NO: 2:

(i) SEQUENCE CHARACTERISTICS:
      (A) LENGTH: 20 amino acids
      (B) TYPE: amino acid
      (C) STRANDEDNESS: <Unknown>
      (D) TOPOLOGY: linear (ii) MOLECULE TYPE: peptide (ix) FEATURE:
      (A) NAME/KEY: Peptide
      (B) LOCATION: 20
      (D) OTHER INFORMATION: /note= "amino acid sequence generated by the 563del63 mutation in the human E-cadherin gene"

(xi) SEQUENCE DESCRIPTION: SEQ ID NO: 2:

Pro Gly Leu Arg Arg Gln Lys Arg Asp Trp Ile Lys Ser Asn Lys Asp
1               5                   10                  15

Lys Glu Gly Lys
            20

(2) INFORMATION FOR SEQ ID NO: 3:

(i) SEQUENCE CHARACTERISTICS:
      (A) LENGTH: 20 amino acids
      (B) TYPE: amino acid
      (C) STRANDEDNESS: <Unknown>
      (D) TOPOLOGY: linear

```
        (ii) MOLECULE TYPE: peptide (ix) FEATURE:
              (A) NAME/KEY: Peptide
              (B) LOCATION: 1..20
              (D) OTHER INFORMATION: /note= "amino acid sequence
                  translated from nucleotides at positions 678 through 737
                  of "normal" human E-cadherin cDNA"

(xi) SEQUENCE DESCRIPTION: SEQ ID NO: 3:

Gln Gly Ala Asp Thr Pro Pro Val Gly Val Phe Ile Ile Glu Arg Glu
1               5                   10                  15

Thr Gly Trp Leu
            20

(2) INFORMATION FOR SEQ ID NO: 4:

(i) SEQUENCE CHARACTERISTICS:
              (A) LENGTH: 20 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Peptide
              (B) LOCATION: 1..20
              (D) OTHER INFORMATION: /note= "amino acid sequence
                  generated by the 706del9 mutation in the human E-cadherin
                  gene"

(xi) SEQUENCE DESCRIPTION: SEQ ID NO: 4:

Gln Gly Ala Asp Thr Pro Pro Val Gly Val Glu Arg Glu Thr Gly Trp
1               5                   10                  15

Leu Lys Val Thr
            20

(2) INFORMATION FOR SEQ ID NO: 5:

(i) SEQUENCE CHARACTERISTICS:
              (A) LENGTH: 20 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Peptide
              (B) LOCATION: 1..20
              (D) OTHER INFORMATION: /note= "amino acid sequence
                  translated from nucleotides at positions 1007 through
                  1066 of "normal" human E-cadherin cDNA"

(xi) SEQUENCE DESCRIPTION: SEQ ID NO: 5:

Leu Ser Gln Asp Pro Glu Leu Pro Asp Lys Asn Met Phe Thr Ile Asn
1               5                   10                  15

Arg Asn Thr Gly
            20

(2) INFORMATION FOR SEQ ID NO: 6:

(i) SEQUENCE CHARACTERISTICS:
              (A) LENGTH: 20 amino acids
              (B) TYPE: amino acid
              (C) STRANDEDNESS: <Unknown>
              (D) TOPOLOGY: linear (ii) MOLECULE TYPE: peptide
```

```
    (ix) FEATURE:
         (A) NAME/KEY: Peptide
         (B) LOCATION: 1..20
         (D) OTHER INFORMATION: /note= "amino acid sequence
             generated by the 1036del15 mutation in the human
             E-cadherin gene"

(xi) SEQUENCE DESCRIPTION: SEQ ID NO: 6:

Leu Ser Gln Asp Pro Glu Leu Pro Asp Lys Asn Arg Asn Thr Gly Val
1               5                  10                  15

Ile Ser Val Val
            20

(2) INFORMATION FOR SEQ ID NO: 7:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (ix) FEATURE:
         (A) NAME/KEY: Peptide
         (B) LOCATION: 20
         (D) OTHER INFORMATION: /note= "amino acid sequence
             translated from nucleotides at positions 1074 through 1133
             of "normal" human E-cadherin cDNA"

(xi) SEQUENCE DESCRIPTION: SEQ ID NO: 7:

Ser Val Val Thr Thr Gly Leu Asp Arg Glu Ser Phe Pro Thr Tyr Thr
1               5                  10                  15

Leu Val Val Gln
            20

(2) INFORMATION FOR SEQ ID NO: 8:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (ix) FEATURE:
         (A) NAME/KEY: Peptide
         (B) LOCATION: 1..20
         (D) OTHER INFORMATION: /note= "amino acid sequence
             generated by the 1103del129 mutation in the human
             E-cadherin gene"

(xi) SEQUENCE DESCRIPTION: SEQ ID NO: 8:

Ser Val Val Thr Thr Gly Leu Asp Arg Glu Tyr Lys Gly Gln Val Pro
1               5                  10                  15

Glu Asn Glu Ala
            20

(2) INFORMATION FOR SEQ ID NO: 9:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide
```

```
   (ix) FEATURE:
        (A) NAME/KEY: Peptide
        (B) LOCATION: 1..20
        (D) OTHER INFORMATION: /note= "amino acid sequence
             translated from nucleotides at positions 1203 through
             1262 of "normal" human E-cadherin cDNA"

(xi) SEQUENCE DESCRIPTION: SEQ ID NO: 9:

Asp Asn Pro Pro Ile Phe Asn Pro Thr Thr Tyr Lys Gly Gln Val Pro
1               5                   10                  15

Glu Asn Glu Ala
            20

(2) INFORMATION FOR SEQ ID NO: 10:

(i) SEQUENCE CHARACTERISTICS:
       (A) LENGTH: 20 amino acids
       (B) TYPE: amino acid
       (C) STRANDEDNESS: <Unknown>
       (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence
             generated by the 1232del183 mutation in the human
             E-cadherin gene"

(xi) SEQUENCE DESCRIPTION: SEQ ID NO: 10:

Asp Asn Pro Pro Ile Phe Asn Pro Thr Thr Gly Leu Asp Phe Glu Ala
1               5                   10                  15

Lys Gln Gln Tyr
            20

(2) INFORMATION FOR SEQ ID NO: 11:

(i) SEQUENCE CHARACTERISTICS:
       (A) LENGTH: 20 amino acids
       (B) TYPE: amino acid
       (C) STRANDEDNESS: <Unknown>
       (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence
             translated from nucleotides at positions 1385 through 1444
             of "normal" human E-cadherin"

(xi) SEQUENCE DESCRIPTION: SEQ ID NO: 11:

Asn Asn Asp Gly Ile Leu Lys Thr Ala Lys Gly Leu Asp Phe Glu Ala
1               5                   10                  15

Lys Gln Gln Tyr
            20

(2) INFORMATION FOR SEQ ID NO: 12:

(i) SEQUENCE CHARACTERISTICS:
       (A) LENGTH: 20 amino acids
       (B) TYPE: amino acid
       (C) STRANDEDNESS: <Unknown>
       (D) TOPOLOGY: linear (ii) MOLECULE TYPE: peptide (ix) FEATURE:
```

(A) NAME/KEY: Peptide
        (B) LOCATION: 1..20
        (D) OTHER INFORMATION: /note= "amino acid sequence
            generated by the 1414del69 mutation in the human
            E-cadherin gene"

(xi) SEQUENCE DESCRIPTION: SEQ ID NO: 12:

Asn Asn Asp Gly Ile Leu Lys Thr Ala Lys Val Ser Leu Thr Thr Ser
1               5                   10                  15

Thr Ala Thr Val
            20

(2) INFORMATION FOR SEQ ID NO: 13:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence at
            positions 360 through 379 of "normal" human E-cadherin
            protein"

(xi) SEQUENCE DESCRIPTION: SEQ ID NO: 13:

Thr Ala Val Ile Thr Val Thr Asp Thr Asn Asp Asn Pro Pro Ile Phe
1               5                   10                  15

Asn Pro Thr Thr
            20

(2) INFORMATION FOR SEQ ID NO: 14:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence
            generated by the Asp370Ala mutation in human E-cadherin
            protein"

(xi) SEQUENCE DESCRIPTION: SEQ ID NO: 14:

Thr Ala Val Ile Thr Val Thr Asp Thr Asn Ala Asn Pro Pro Ile Phe
1               5                   10                  15

Asn Pro Thr Thr
            20

(2) INFORMATION FOR SEQ ID NO: 15:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide (B) LOCATION: 1..20
(D) OTHER INFORMATION: /note= "amino acid sequence at
    positions 463 through 482 of "normal" human E-cadherin
    protein"

(xi) SEQUENCE DESCRIPTION: SEQ ID NO: 15:

```
Glu Val Ser Leu Thr Thr Ser Thr Ala Thr Val Thr Val Asp Val Leu
1               5                   10                  15

Asp Val Asn Glu
            20
```

(2) INFORMATION FOR SEQ ID NO: 16:

(i) SEQUENCE CHARACTERISTICS:
  (A) LENGTH: 20 amino acids
  (B) TYPE: amino acid
  (C) STRANDEDNESS: <Unknown>
  (D) TOPOLOGY: linear (ii) MOLECULE TYPE: peptide (ix) FEATURE:
  (A) NAME/KEY: Peptide
  (B) LOCATION: 1..20
  (D) OTHER INFORMATION: /note= "amino acid sequence
   generated by the Val473Asp mutation in human E-cadherin
   protein"

(xi) SEQUENCE DESCRIPTION: SEQ ID NO: 16:

```
Glu Val Ser Leu Thr Thr Ser Thr Ala Thr Asp Thr Val Asp Val Leu
1               5                   10                  15

Asp Val Asn Glu
            20
```

(2) INFORMATION FOR SEQ ID NO: 17:

(i) SEQUENCE CHARACTERISTICS:
  (A) LENGTH: 20 amino acids
  (B) TYPE: amino acid
  (C) STRANDEDNESS: <Unknown>
  (D) TOPOLOGY: linear (ii) MOLECULE TYPE: peptide (ix) FEATURE:
  (A) NAME/KEY: Peptide
  (B) LOCATION: 1..20
  (D) OTHER INFORMATION: /note= "amino acid sequence at
   positions 588 through 607 of "normal" human E-cadherin
   protein"

(xi) SEQUENCE DESCRIPTION: SEQ ID NO: 17:

```
Val Asn Asp Asn Ala Pro Ile Pro Glu Pro Arg Thr Ile Phe Phe Cys
1               5                   10                  15

Glu Arg Asn Pro
            20
```

(2) INFORMATION FOR SEQ ID NO: 18:

(i) SEQUENCE CHARACTERISTICS:
  (A) LENGTH: 20 amino acids
  (B) TYPE: amino acid
  (C) STRANDEDNESS: <Unknown>
  (D) TOPOLOGY: linear (ii) MOLECULE TYPE: peptide (ix) FEATURE:
  (A) NAME/KEY: Peptide
  (B) LOCATION: 1..20

(D) OTHER INFORMATION: /note= "amino acid sequence
            generated by the Arg598Gln mutation in human E-cadherin
            protein"

(xi) SEQUENCE DESCRIPTION: SEQ ID NO: 18:

Val Asn Asp Asn Ala Pro Ile Pro Glu Pro Gln Thr Ile Phe Phe Cys
1               5                   10                  15

Glu Arg Asn Pro
        20

(2) INFORMATION FOR SEQ ID NO: 19:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..19
        (D) OTHER INFORMATION: /note= "amino acid sequence
            translated from nucleotides at positions 795 through 854
            of "normal" human E-cadherin cDNA"

(xi) SEQUENCE DESCRIPTION: SEQ ID NO: 19:

Ala Val Ser Ser Asn Gly Asn Ala Val Glu Asp Pro Met Glu Ile Leu
1               5                   10                  15

Ile Thr Val (2) INFORMATION FOR SEQ ID NO: 20:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence
            generated by the 826del9 mutation in the human E-cadherin
            gene"

(xi) SEQUENCE DESCRIPTION: SEQ ID NO: 20:

Ala Val Ser Ser Asn Gly Asn Ala Val Glu Glu Ile Leu Ile Thr Val
1               5                   10                  15

Thr Asp Gln Asn
        20

(2) INFORMATION FOR SEQ ID NO: 21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "primer ATG"

(xi) SEQUENCE DESCRIPTION: SEQ ID NO: 21:

ATGGGCCCTT GGAGCCG                                                          17

(2) INFORMATION FOR SEQ ID NO: 22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "primer Ex 8"

(xi) SEQUENCE DESCRIPTION: SEQ ID NO: 22:

CTACGTATAC CCTGGTGG                                                         18

(2) INFORMATION FOR SEQ ID NO: 23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..21
        (D) OTHER INFORMATION: /note= "primer Ex9/1"

(xi) SEQUENCE DESCRIPTION: SEQ ID NO: 23:

TACAAGGGTC AGGTGCCTGA G                                                     21

(2) INFORMATION FOR SEQ ID NO: 24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "primer rEx 10"

(xi) SEQUENCE DESCRIPTION: SEQ ID NO: 24:

GGGGGCTTCA TTCACATC                                                         18

(2) INFORMATION FOR SEQ ID NO: 25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "primer r3'/2/neu"

(xi) SEQUENCE DESCRIPTION: SEQ ID NO: 25:

CCAGCACATG GGTCTGGG                                                         18

(2) INFORMATION FOR SEQ ID NO: 26:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..18
            (D) OTHER INFORMATION: /note= "primer Ex7"

(xi) SEQUENCE DESCRIPTION: SEQ ID NO: 26:

ACCTCTGTGA TGGAGGTC                                                         18

(2) INFORMATION FOR SEQ ID NO: 27:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..24
            (D) OTHER INFORMATION: /note= "primer rEx11"

(xi) SEQUENCE DESCRIPTION: SEQ ID NO: 27:

TGTGTACGTG CTGTTCTTCA CGTG                                                  24

(2) INFORMATION FOR SEQ ID NO: 28:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..20
            (D) OTHER INFORMATION: /note= ""forward" primer ATG"

(xi) SEQUENCE DESCRIPTION: SEQ ID NO: 28:

CCATGGGCCC TTGGAGCCGC                                                       20

(2) INFORMATION FOR SEQ ID NO: 29:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..22

(D) OTHER INFORMATION: /note= ""reverse" primer rEx6"

(xi) SEQUENCE DESCRIPTION: SEQ ID NO: 29:

CTGGAAGAGC ACCTTCCATG AC                                              22

(2) INFORMATION FOR SEQ ID NO: 30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..24
        (D) OTHER INFORMATION: /note= ""forward" primer Ex5"

(xi) SEQUENCE DESCRIPTION: SEQ ID NO: 30:

ACAGAGCCTC TGGATAGAGA ACGC                                            24

(2) INFORMATION FOR SEQ ID NO: 31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= ""reverse" primer rEx10/2"

(xi) SEQUENCE DESCRIPTION: SEQ ID NO: 31:

CCACATTCGT CACTGCTACG                                                 20

(2) INFORMATION FOR SEQ ID NO: 32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= ""forward" primer Ex9/2a"

(xi) SEQUENCE DESCRIPTION: SEQ ID NO: 32:

CAGCGTGGGA GGCTGTATAC AC                                              22

(2) INFORMATION FOR SEQ ID NO: 33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -

(B) LOCATION: 1..21
        (D) OTHER INFORMATION: /note= ""reverse" primer rEx11"

(xi) SEQUENCE DESCRIPTION: SEQ ID NO: 33:

TGTGTACGTG CTGTTCTTCA C                                              21

(2) INFORMATION FOR SEQ ID NO: 34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..21
        (D) OTHER INFORMATION: /note= ""forward" primer Ex10/2"

(xi) SEQUENCE DESCRIPTION: SEQ ID NO: 34:

GTGTCCGAGG ACTTTGGCGT G                                              21

(2) INFORMATION FOR SEQ ID NO: 35:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..25
        (D) OTHER INFORMATION: /note= ""reverse" primer rEx13"

(xi) SEQUENCE DESCRIPTION: SEQ ID NO: 35:

TCAGAATTAG CAAAGCAAGA ATTCC                                          25

(2) INFORMATION FOR SEQ ID NO: 36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..21
        (D) OTHER INFORMATION: /note= ""forward" primer Ex13"

(xi) SEQUENCE DESCRIPTION: SEQ ID NO: 36:

GGCGTCTGTA GGAAGGCACA G                                              21

(2) INFORMATION FOR SEQ ID NO: 37:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:

(A) NAME/KEY: -
        (B) LOCATION: 1..18
        (D) OTHER INFORMATION: /note= ""reverse" primer r3prime"

(xi) SEQUENCE DESCRIPTION: SEQ ID NO: 37:

CCAGCACATG GGTCTGGG                                                     18

(2) INFORMATION FOR SEQ ID NO: 38:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /note= "sequence region generated
              by mutation 563del63"

(xi) SEQUENCE DESCRIPTION: SEQ ID NO: 38:

CCTGGCCTCA GAAGACAGAA GAGAGACTGG ATCAAATCCA ACAAAGACAA AGAAGGCAAG      60

(2) INFORMATION FOR SEQ ID NO: 39:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /note= "sequence region generated
              by mutation 706del9"

(xi) SEQUENCE DESCRIPTION: SEQ ID NO: 39:

CAAGGAGCTG ACACACCCCC TGTTGGTGTT GAAAGAGAAA CAGGATGGCT GAAGGTGACA      60

(2) INFORMATION FOR SEQ ID NO: 40:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /note= "sequence region generated
              by mutation 1036del15"

(xi) SEQUENCE DESCRIPTION: SEQ ID NO: 40:

CTCAGCCAAG ATCCTGAGCT CCCTGACAAA AACAGGAACA CAGGAGTCAT CAGTGTGGTC      60

(2) INFORMATION FOR SEQ ID NO: 41:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
            (A) NAME/KEY: -
            (B) LOCATION: 1..60
            (D) OTHER INFORMATION: /note= "sequence region generated
                by mutation 1103del129"

(xi) SEQUENCE DESCRIPTION: SEQ ID NO: 41:

AGTGTGGTCA CCACTGGGCT GGACCGAGAG TACAAGGGTC AGGTGCCTGA GAACGAGGCT    60

(2) INFORMATION FOR SEQ ID NO: 42:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..60
            (D) OTHER INFORMATION: /note= "sequence region generated
                by mutation 1232del183"

(xi) SEQUENCE DESCRIPTION: SEQ ID NO: 42:

GATAATCCTC CGATCTTCAA TCCCACCACG GGCTTGGATT TTGAGGCCAA GCAGCAGTAC    60

(2) INFORMATION FOR SEQ ID NO: 43:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..60
            (D) OTHER INFORMATION: /note= "sequence region generated
                by mutation 1414del69"

(xi) SEQUENCE DESCRIPTION: SEQ ID NO: 43:

AACAACGATG GCATTTTGAA AACAGCAAAG GTNTCTCTCA CCACCTCCAC AGCCACCGTC    60

(2) INFORMATION FOR SEQ ID NO: 44:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..60
            (D) OTHER INFORMATION: /note= "sequence region generated
                by mutation Asp370Ala"

(xi) SEQUENCE DESCRIPTION: SEQ ID NO: 44:

ACAGCTGTGA TCACAGTCAC TGACACCAAC GCTAATCCTC CGATCTTCAA TCCCACCACG    60

(2) INFORMATION FOR SEQ ID NO: 45:

```
    (i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /note= "sequence region generated
             by mutation Val473Asp"

(xi) SEQUENCE DESCRIPTION: SEQ ID NO: 45:

GAGGTCTCTC TCACCACCTC CACAGCCACC GACACCGTGG ATGTGCTGGA TGTGAATGAA    60

(2) INFORMATION FOR SEQ ID NO: 46:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /note= "sequence region generated
             by mutation Arg598Gln"

(xi) SEQUENCE DESCRIPTION: SEQ ID NO: 46:

GTGAATGACA ACGCCCCCAT ACCAGAACCT CAAACTATAT TCTTCTGTGA GAGGAATCCA    60

(2) INFORMATION FOR SEQ ID NO: 47:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /note= "sequence region generated
             by mutation 826del9"

(xi) SEQUENCE DESCRIPTION: SEQ ID NO: 47:

GCTGTGTCAT CCAACGGGAA TGCAGTTGAG GAGATTTTGA TCACGGTAAC CGATCAGAAT    60

(2) INFORMATION FOR SEQ ID NO: 48:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..13
        (D) OTHER INFORMATION: /note= "amino acid sequence
             generated by the mutation 1232del183 in the human
             E-cadherin gene"
```

```
(xi) SEQUENCE DESCRIPTION: SEQ ID NO: 48:

Pro Ile Phe Asn Pro Thr Thr Gly Leu Asp Phe Glu Ala
1               5                   10
```

MUTATIONS OF E CADHERIN AS A BASIS FOR THE DIAGNOSIS AND THERAPY OF HUMAN MALIGNANT TUMORS

CROSS REFERENCE TO RELATED APPLICATIONS

The present application claims priority to and is a continuation in part of U.S. Ser. No. 08/899,279, filed Jul. 23, 1997, now U.S. Pat. No. 6,447,776, which claims priority to German patent application No. DE 196 29 938.1, filed Jul. 24, 1996, herein each incorporated by reference in their entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The invention relates to monoclonal antibodies specifically directed against mutated transmembrane E-cadherin and useful for the detection and therapy of gastric carcinomas.

BACKGROUND OF THE INVENTION

Introduction

Statistical evaluations of the causes of death show malignant tumors to be in a front position worldwide. Among these tumors the gastric carcinoma internationally takes the second position of tumors resulting in death. Several genetic alterations have been reported in association with the gastric carcinoma including microsatellite instabilities and alterations of the genes p53, APC DCC (Tahara E: Genetic alterations in human gastrointestinal cancers. Cancer 1995; 75:1410–1417). Histomorphologically, two types of gastric carcinoma can be distinguished (Laurén P: The two histological main types of gastric carcinoma: diffuse and so-called intestinal-type of carcinoma. Acta Pathol. Microbiol. Scand. 1965; 64:31–49): one type are the intestinal carcinomas having a glandular differentiation, the other type consists of diffuse carcinomas with disrupted tissue architecture. So far, the genetic basis for this bipartite development and morphology has not been clarified. Possibly, alterations in the E-cadherin molecule may be of importance in this respect. E-cadherin is a homophilic transmembrane cellular adhesion molecule playing a key role in the interaction of epithelial tissues. Initial molecular-biological studies of the E-cadherin gene comprising 16 exons indicated that mutations may contribute to the morphology and growth type of gastric carcinomas (Becker K-F, Atkinson M J, Reich U, Becker I, Nekarda H, Siewert J R, Höfler H: E-cadherin gene mutations provide clues to diffuse type gastric carcinomas. Cancer Res. 1994; 54(14):3845–3852).

Basically, alterations of malignant tumors are of interest for the explanation of certain biological patterns of behaviour; these phenomenons may be used as a specific characteristic feature and, therefore, as a tumor marker. These characteristics include cellular products and also typical properties of the cell surface which can be assessed in a direct or indirect manner. To date, the isolation of a surface antigen or cellular product restricted solely to tumor cells has not been successful. Up to now the increased occurrence of certain cellular properties (surface antigen, intracellular proteins, secreted cellular products) in the body relative to normal tissue has been used as the basis for diagnosis and therapy of malignant diseases.

State of the use of E-cadherin in diagnosis and therapy

The first publications reported that E-cadherin—detected by immunohistochemistry using specific antibodies—showed an altered expression pattern in tumor cells. The immunoreactivity of E-cadherin was partly reduced in or absent from tumor tissue (see Table 1). Other authors thought this fact to be the reason for a decreased production ("downregulation") of the protein in the tumor (cf. Birchmeier, DE-A-41 10 405 A1).

TABLE 1

E-cadherin immunoreactivity in patients suffering from gastric carcinoma

| Histology | $n^a$ | E-cadherin immunoreactivity unchanged$^b$ | abnormal$^c$ | Reference |
|---|---|---|---|---|
| diffuse | 28 | 13 (46%) | 15 (54%) | 1 |
| intestinal | 93 | 69 (74%) | 24 (26%) | 1 |
| diffuse | 14 | 7 (50%) | 7 (50%) | 2 |
| intestinal | 22 | 21 (95%) | 1 (5%) | 2 |
| diffuse | 11 | 6 (55%) | 5 (45%) | 3 |
| diffuse | 21 | 0 | 21 (100%) | 4 |
| intestinal | 30 | 5 (17%) | 25 (83%) | 4 |
| diffuse | 27 | 19 (70%) | 8 (30%) | 5 |
| intestinal | 17 | 17 (100%) | 0 | 5 |

Legend of Table 1:
$^a$Number of patients examined;
$^b$immunoreactivity of E-cadherin similar to "normal" tissue;
$^c$E-cadherin immunoreactivity in the tumor decreased or not present.

References for Table 1.

1 Shino Y, Watanabe A, Yamada Y, Tanase M, Yamada T, Matsuda M, Yamashita J, Tatsumi M, Miwa T, Nakano H: Clinicopathologic evaluation of immunohistochemical E-cadherin Expression in human gastric carcinomas. Cancer 1995; 76:2193–2201.
2 Brito M J, Jacinto L, Jankowski J, Pignatelli M, Filipe MI: E-cadherin (cell adhesion molecule) in gastric carcinoma. Path. Res. Pract. 1995; 191:628 [Abstract].
3 Matsui S, Shiozaki H, Inoue M, Tamura S, Doki Y, Kadowaki T, Iwazawa T, Shimaya K, Nagafuchi A, Tsukita S, Mori T: Immunohistochemical evaluation of alpha-catenin expression in human gastric cancer. Virchows Archiv 1994; 424:375–381.
4 Mayer B, Johnson J P, Leitl F, Jauch K W, Heiss M M, Schildberg F W, Birchmeier W, Funke I: E-cadherin expression in primary and metastatic gastric cancer: down-regulation correlates with cellular dedifferentiation and glandular disintegration. Cancer Res. 1993; 53:1690–1695.
5 Shimoyama Y, Hirohashi S: Expression of E- and P-cadherin in gastric carcinomas. Cancer Res. 1991; 51(8):2185–2192.

Our own considerations regarding these phenomena aimed for the first time at the integrity of the E-cadherin gene. After RNA extraction, reverse transcription and direct DNA sequencing, the molecular-biological examination of gastric carcinoma tissue revealed defects in the E-cadherin gene. Gastric carcinomas of the diffuse subtype were examined for genetic alterations in a part of the E-cadherin gene (exons 6–10 and 13–16). Loss of exons 8 and 9, partial loss of exon 10, or a point mutation in the region of exon 8 were observed (Becker K-F, Atkinson M J, Reich U, Becker I, Nekarda H, Siewert J R, Höfler H: E-cadherin gene mutations provide clues to diffuse type gastric carcinomas. Cancer Res. 1994; 54(14):3845–3852). Tumors of the intestinal subtype showed no mutations leading to structural alterations. Analysis of the found mutations revealed that individual deletions occurred with somewhat higher frequency, but also point mutations or smaller deletions could be observed. Immunohistochemical staining (antibody: HECD-1, Takara Biomedicals, Japan, cf. methodology section) of some of the cases with mutated E-cadherin predominantly showed a transmembrane staining of the tumor cells and also staining of non-tumorous mucosa. We were not able to distinguish whether the labeling of the tumor cells corresponded to the detection of wildtype E-cadherin or mutated E-cadherin. On the one hand, there was the possibility that mutated protein continued to be incorporated into the cellular membrane and that the antibody against E-cadherin (HECD-1) recognizes an epitope apart from the mutated region. A further explanation could be the binding of the antibody to wildtype E-cadherin which—being generated by the second, not mutated allele—is also expressed in tumor cells. Initially, the fact that some of the tumors showed no staining led us to suggest the presence of further mutations apart from the examined exons 6–10 and 13–16 which might have an influence on the translation or the stability of the protein.

SUMMARY OF THE INVENTION

It is an object of the present invention to provide monoclonal antibodies which are specifically suitable for the detection and therapy of gastric carcinomas and in particular diffuse gastric carcinomas.

It is a further object of the present invention to provide methods for the detection and therapy of diffuse gastric carcinomas.

This object is achieved according to the invention by the monoclonal antibodies characterized in more detail in claim 1. Preferred embodiments of the invention follow from the dependent as well as the secondary claims.

The analysis of regions of the E-cadherin gene which have not been examined so far (exons 1–5, 11, and 12), and the sequencing of the cDNA of E-cadherin of ten additional cases of diffuse gastric carcinoma revealed further mutations in diffuse gastric carcinoma (cf. the "Methodology" section). These newly found mutations (Table 2) surprisingly continued to show a typical pattern. In all of the cases, these mutations were either multimers of a base triplet not affecting the reading frame or they were point mutations. By these studies we were able to exclude the suggestion made after immunohistochemical examination that the loss of the immunoreactivity may be caused by translation-disrupting mutations. In parallel to the examination of gastric carcinomas also other epithelial tumors were analysed. None of the cases of mamma carcinoma, oesophagus carcinoma, and large intestinal carcinoma showed patterns corresponding to those of gastric carcinoma.

TABLE 2

E-cadherin mutations in gastric carcinoma found by us.

| Mutation | Exon | Nucleotide position | Amino Acid(s) | Type of mutation |
|---|---|---|---|---|
| 563del63 | 4 | 563 | Amino acids 157–177 | in-frame deletion of 63 bp |
| 706del9 | 5 | 706 | 205–207 | in-frame deletion of 9 bp |
| 826del9 | 6 | 826 (T to G) | 245–247; 244 (Asp to Glu) | in-frame deletion of 9 bp and missense mutation |
| 1036del15 | 7 | 1036 | 315–319 | in-frame deletion of 15 bp |
| 1103del129 | 8 | 1103 | 337–379 | in-frame deletion of 129 bp (complete loss of exon 8) |
| Asp370Ala | 8 | 1203 | 370 (Asp to Ala) | Missense mutation |
| 1232del183 | 9 | 1232 | 380–440 | in-frame deletion of 183 bp (complete loss of exon 9) |
| 1414del69 | 10 | 1414 | 441–463 | in-frame deletion of 69 bp |
| Val473Asp | 10 | 1512 | 473 (Val to Asp) | Missense mutation |
| Arg598Gln | 12 | 1887 | 598 (Arg to Gln) | Missense mutation |

Additional studies carried out with respect to the characteristics of the mutations as well as sequencing of additional tumors now have led to a principle which has not yet been reported and is unique in the case of carcinomas: the alterations of E-cadherin in diffuse gastric carcinoma are in-frame mutations (and not disruptions of the reading frame). This result is useful for diagnostic and therapeutic purposes, for example the therapeutic use of antibodies, which recognize mutant E-cadherin amino acid sequences.

As far as these therapeutic uses are concerned, the use of radiolabeled MAbs (monoclonal antibodies) in radioimmuno-therapy has been limited up to now because of the lack of tumor-specific antigens. In most cases reported thus far, tumor antigens that serve as targets are not tumor-specific, being overexpressed by tumor cells and also at a lower level by normal cells. Thus far, only one tumor-specific MAb has been reported that recognizes a mutant form of the epidermal growth factor receptor (EGFR vIII) that is found on different tumor types but not on normal human tissue (1). This antibody has been labeled with $^{125}$I, $^{131}$I, and the α-emitter $^{211}$At, and it appears to be a promising candidate for radioimmunotherapy (2, 3).

BRIEF DESCRIPTION OF THE DRAWINGS

The invention will in the following be explained in more detail with respect to the Figures. The Figures show:

FIGS. 7A–C. An example of the development of i.p. carcinomatosis with ascites 5 weeks after injection of 1×10$^7$ cells expressing mutant E-cadherin.

(A) macroscopic view showing development of small tumor nodules in the peritoneum (arrow).
(B) histological section of an i.p. nodule with tumor cells on the serosa (arrow head) and invasive tumor cells in the mesenteric adipose tissue (arrow; 3200; H&E staining).
(C) single tumor cells (arrow heads) and small cell clusters (arrow) in the ascites fluid with a nonspecific inflammatory reaction(3400; modified May-Grünwald-Giemsa staining).

FIGS. 8A–B. Autoradiographies of an 8-μm tumor section 1 h after intratumoral injection of $^{213}$Bi-d9MAb in a tumor expressing mutant E-cadherin (A) and in wild type E-cadherin tumors (B).

(A) Autoradiography of an 8-μm tumor section 1 h after intratumoral injection of $^{213}$Bi d9MAb in a tumor expressing mutant E-cadherin (activity retention at the three injection sites in the center of the tumor [arrow heads] and at the puncture sites at the tumor periphery [arrows]).
(B) Autoradio-graphy of a 8 μm tumor section, 1 h after intratumoral injection of a $^{213}$Bi-d9MAb in wild type E-cadherin tumors (no specific activity retention).

FIGS. 9A–C. Scintigrams of mice 48 h after i.p. injection of 740 kBq (20 μCi) $^{111}$In-d9MAb. Scintigrams of mice 48 h after i.p. injection of 740 kBq (20 μCi) $^{111}$In d9MAb.

(A) Mouse without tumor cell injection showing blood pool mainly in the heart, lungs, and liver; no visible retention of activity in the peritoneal cavity.
(B) Mouse with tumors expressing mutant E-cadherin; besides some blood pool activity, there is a clearly visible activity accumulation in peritoneal tumor nodules (arrows).
(C) Mouse with i.p. tumors expressing wild-type E-cadherin showing blood pool mainly as in (A).

DETAILED DESCRIPTION OF THE INVENTION

Figure 1:
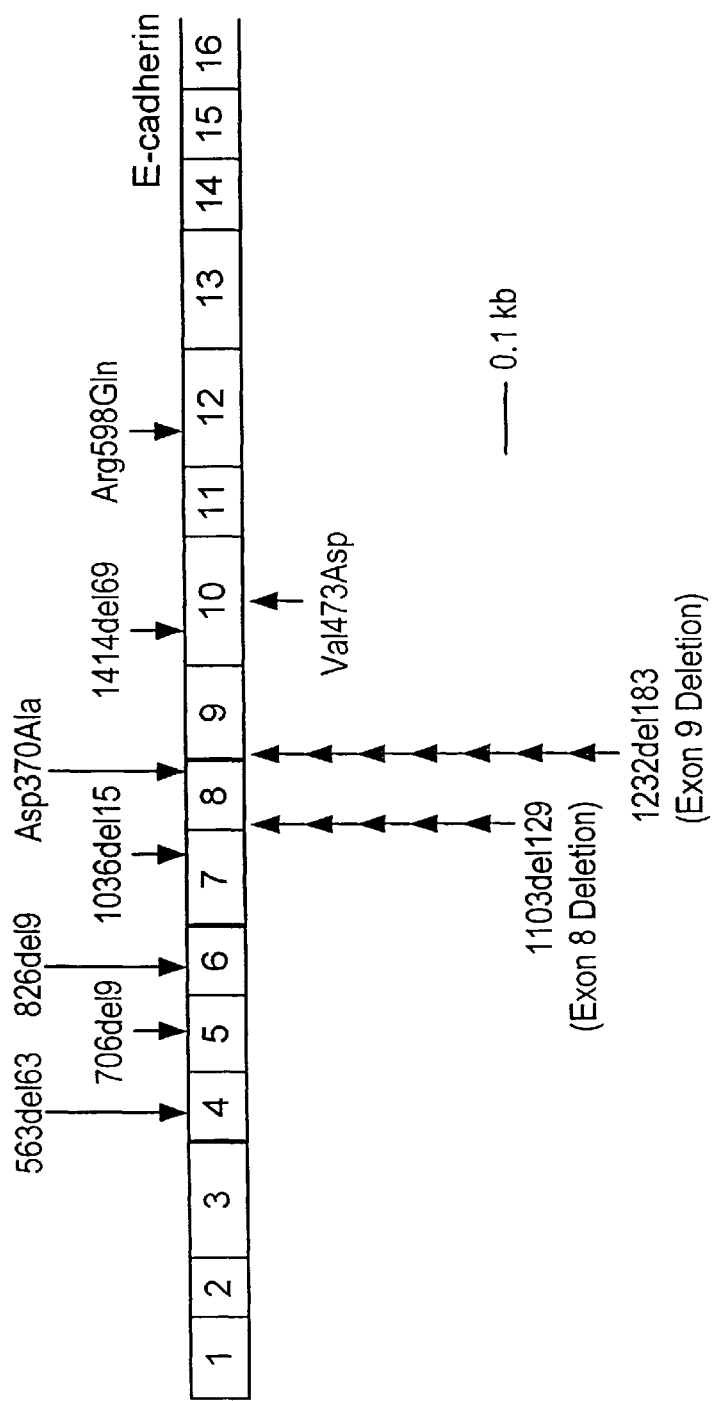
FIG. 1. A review of the E-cadherin mutations in diffuse gastric carcinoma known so far which typically represent in-frame deletions. The mutations are presented as follows: arrows denote a detected mutation; the translated E-cadherin sequence is shaded; numbered boxes represent exons; an amino acid followed by a codon position denotes a "missense mutation"; a number without prefix indicates the localisation of a deletion (del), the figure after "del" being the number of base pairs missing.

We have been successful in providing evidence for a typical form of mutation—in-frame mutations (deletions of multimers of a base triplet or point mutations, respectively)—in the case of the diffuse gastric carcinoma (see FIG. 1).

These characteristic mutations enable us to conclude that an altered protein is generated in all of the cases and is further expressed by the cell. Evidence for this suggestion has been gained by transfection of the mutated genes into a cell line deficient for E-cadherin (MDA mamma carcinoma cells) (see Annex for methodology). Stably transfected cells expressed the mutated protein at the cellular membrane; the membraneous localisation of the mutated protein has been unequivocally proven by means of immunofluorescence (FIG. 2) and electron microscopy (FIG. 3) using the exon 9 deletion as an example. The undisturbed membraneous localisation of the mutated protein is of critical importance for its further use in diagnosis and therapy.

The loss of base sequences or the presence of point mutations, respectively, generate a new, unique and unmistakable RNA sequence while the continuity of transcription is maintained. This "mistake" is then anchored in the protein by an altered amino acid sequence in the course of the subsequent translation. The new protein sequences generated by the mutation are listed in detail in Table 3.

Individual tumor cells are unmistakably labeled by these sequences, i.e. by their mutated E-cadherin gene. A search (comparison of homology) carried out in several gene data banks (via EMBL/GenBank/SWISS-PROT/PDB, Release 32.0) provided no similarity to any sequences known up to now. Early gastric carcinomas were examined with regard to the clonality of the mutation event. Since also in these cases mutations could be detected (own observations) mutations in E-cadherin must be an early event in the course of tumor development, possibly going back to the original malignant clone.

TABLE 3

Newly generated E-cadherin protein sequences by mutations

| Mutation | "Normal" E-cadherin sequence | SEQ ID No. | New E-cadherin sequence | SEQ ID No. |
| --- | --- | --- | --- | --- |
| 563del63 | PGLRRQKRDW/VIPPISCPEN | 1 | PGLRRQKRDW/IKSNKDKEGK | 2 |
| 706del9 | QGADTPPVGV/FIIERETGWL | 3 | QGADTPPVGV/ERETGWLKVT | 4 |
| 1036del15 | LSQDPELPDK/NMFTINRNTG | 5 | LSQDPELPDK/NRNTGVISVV | 6 |
| 1103del129 | SVVTTGLDRE/SFPTYTLVVQ | 7 | SVVTTGLDRE/YKGQVPENEA | 8 |
| 1232del183 | DNPPIFNPTT/YKGQVPENEA | 9 | DNPPIFNPTT/GLDFEAKQQY | 10 |
| 1414del69 | NNDGILKTAK/GLDFEAKQQY | 11 | NNDGILKTAK/VSLTTSTATV | 12 |

TABLE 3-continued

Newly generated E-cadherin protein sequences by mutations

| Mutation | "Normal" E-cadherin sequence | SEQ ID No. | New E-cadherin sequence | SEQ ID No. |
|---|---|---|---|---|
| Asp370Ala | TAVITVTDTNDNPPIFNPTT | 13 | TAVITVTDTNANPPIFNPTT | 14 |
| Val473Asp | EVSLTTSTATVTVDVLDVNE | 15 | EVSLTTSTATDTVDVLDVNE | 16 |
| Arg598Gln | VNDNAPIPEPRTIFFCERNP | 17 | VNDNAPIPEPQTTFFCERNP | 18 |
| 826del9 | AVSSNGNAVED/PMEILITV | 19 | AVSSNGNAVE/ILITVTDQN | 20 |

The dash (/) shows the position of a deletion; the protein sequence is altered starting from this position; underlined and bold letters indicate amino acids changed by point mutations.

The E-cadherin mutations shown in Table 3 as well as further yet unknown mutations can be used for diagnostic and therapeutic purposes for example as follows:

Rapid RNA Extraction and Subsequent Detection of the Mutation by PCR

The characteristic feature of the mutations described (mainly deletions!) is excellently suitable for a rapid specific test: the amplification of a section of the cDNA by suitable primers (see methodology) embracing the mutated exon regions—in combination with a rapid RNA extraction (see methodology)—allow for the clinical utilisation of the invention (time factor!). The detection in this case can be performed on tissues (e.g. biopsies, punctates, cytologies) and body fluids (e.g. blood).

Figure 4:
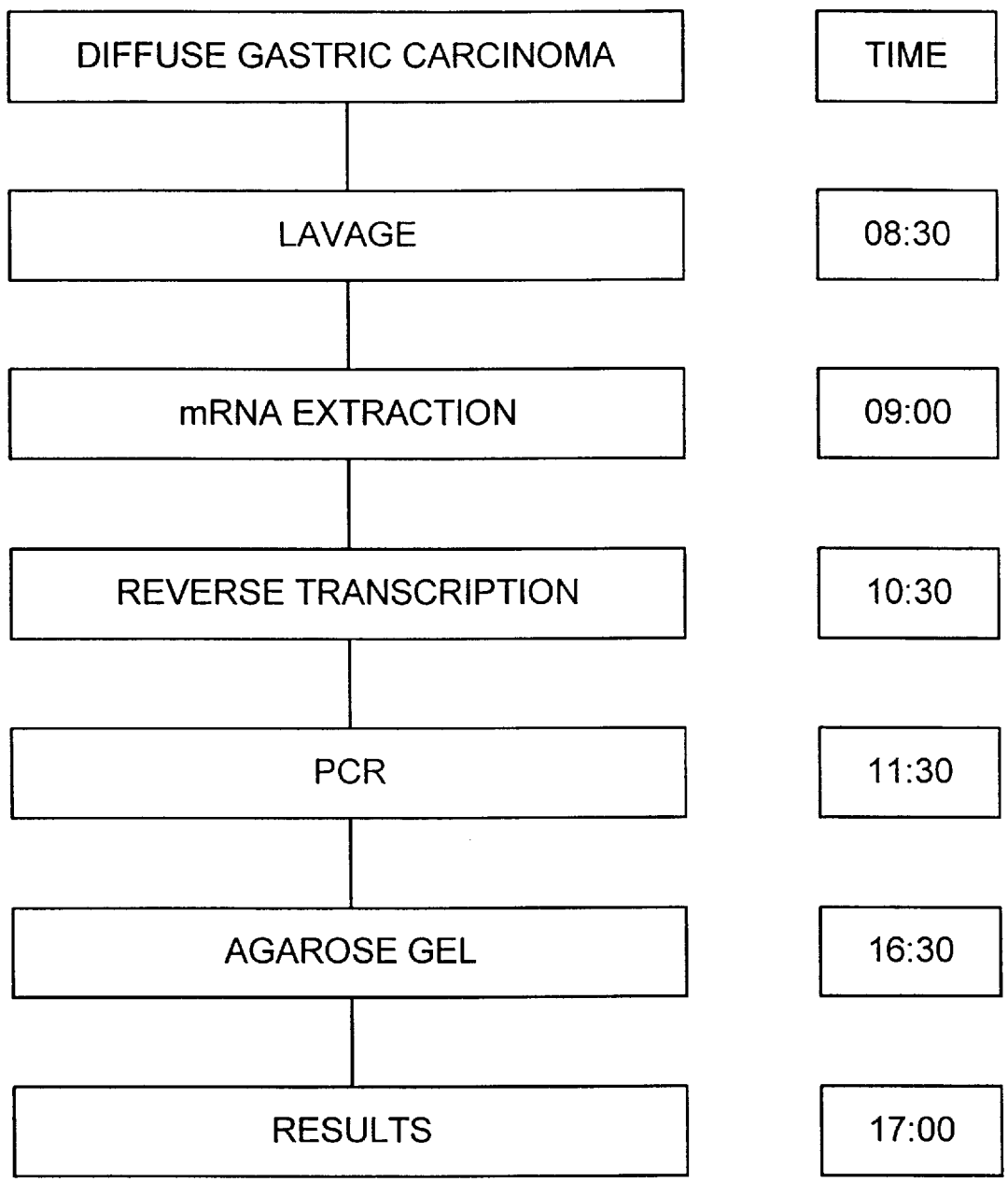
FIG. 4. A flow diagram of the rapid diagnosis of E-cadherin mutations according to the invention.

As an example, biopsies and peritoneal lavages of gastric carcinoma patients were examined for mutations of the E-cadherin gene. Within 8 hours (see FIG. 4) it is possible to specifically determine an alteration in E-cadherin and thereby to provide in-time information for clinical problems. Hereby, seen in the context of the further explanations (see antibodies/therapy) it will be possible to rapidly affect a treatment plan. Basically, this methodology may also be used for the specific initial detection of a gastric carcinoma. Also, it is possible to use it in differential diagnosis (e.g. biopsy of metastases) of other malignomas in the case of an unknown primary tumor (e.g. mamma carcinomas).

Antibodies

The combination of the membraneous localisation and the tumor specificity of the mutated E-cadherin protein allowed for the first time the specific production of a monoclonal antibody exclusively directed against tumor cells.

Figure 5:
FIG. 5. Western blot stained by mutation-specific E-cadherin antibody 7E6.

By the tumor-specific gene sequences provided by the invention it is possible for the first time to detect amino acids the sequence of which stands for a corresponding protein being restricted exclusively to tumor cells. By this, it is possible to generate antibodies selectively directed against the mutated region of E-cadherin. To verify this hypothesis, we attempted to produce examparily a monoclonal antibody against the shortened transmembrane protein via the newly generated sequence using the exon 9 deletion as an example (see Annex for methodology). In this case it was not clear whether the mutated region would be suitable as an antigenic determinant since the sterical arrangement of this epitope is unknown. 23 hybridomas (antibody-producing clones) were generated, and their specificity was tested in vitro (see Annex). One clone (7E6-1) was found which recognizes exon 9-deleted E-cadherin protein on a Western blot and by immunofluorescence. 7E6 antibody fails to detect "normal" E-cadherin (FIG. 5). This cell line producing the 7E6 antibody has been deposited at the DSM (Deposit No. DSM ACC 2277) (Reference Mark: delta CAD-9, clone 7E6-1). The 7E6 antibody recognizes the mutation 1232del183.

Figure 6:
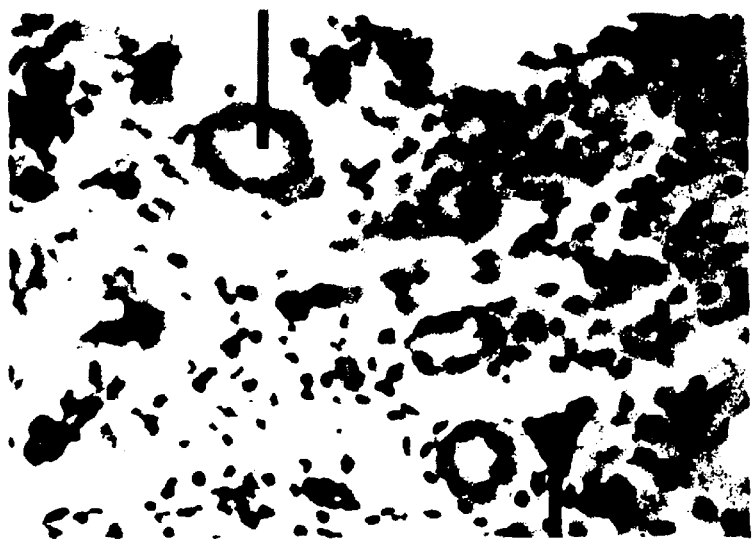
FIG. 6. Immunohistochemistry stained by mutation-specific E-cadherin antibody 7E6.

It could not be expected that this antibody would be functional with regard to material fixed in formalin and embedded in paraffin. For the first time, this allowed for the specific detection of tumor cells on a histological section by means of immunohistochemical methods (FIG. 6). Non-tumorous cells on the same section were not labeled! Thereby, it has become possible to assign the mutated molecule to individual cells. According to our knowledge, a tumor marker with comparable specificity has not yet been described.

The hybridoma cell line deposited at the DSM under the deposit No. ACC 2277 represents merely an example for a cell line producing the monoclonal antibodies provided by the invention. According to the invention, additional antibodies have been already produced which recognize the in-frame mutations. To provide these antibodies is well within the skills of a person skilled in the art working in this field. The 7E6 monoclonal antibody as well as any other antibody generated specifically directed against E-cadherin mutations can be used in diagnosis and therapy as described in the following.

Diagnostics Using Mutation-Specific E-cadherin Antibodies

Retrospective examination of formalin-fixed and paraffin-embedded tissue regarding defects in E-cadherin by means of immunohistochemistry.

Prospective in Vitro Examination of

Blood for the detection of circulating tumor cells as a basic screening for diffuse gastric CA for the evaluation of the pre-, intra-, and post-operative dissemination of tumor cells as possible markers for the course of the disease.

Tumor biopsy for the pre-therapeutic detection of mutated E-cadherin with regard to a plan for a pre-operative (neoadjuvant), intra-operative (peritoneum, portal vein) and post-operative (additive or adjuvant) therapy.

OP preparation for the determination of tumor cells (e.g. edge of removal, ensuring the extent of resection)

Lymph nodes for the detection of metastases and tumor cells ("microenvolvement")

Lavage for the determination of disseminated tumor cells in the peritoneal cavity
Tissue for the determination of disseminated tumor cells (immunohistochemistry)
Differential diagnosis of carcinomas immunohistochemical determination of characteristic E-cadherin mutations for differential diagnostic evaluation of suspected tissue samples
Screening of high-risk groups ("cancer families") determination of E-cadherin mutations in blood cells (DNA)
in vivo Prerequisite: humanisation of the antibody for therapeutic use specific determination of tumor cells by immunoscintigraphy: pre-therapeutically for set up of operation plan/therapy plan for the control of the course of therapy or, respectively, for the verification of a successful therapy and for the control of the post-therapeutical course of the disease Therapy by Mutation-Specific E-cadherin Antibodies immunoradiotherapy
  coupling of a source of radiation to the mutation-specific antibody
immunotoxin therapy
  coupling of a toxin (e.g. pseudomonas toxin) to the antibody Somatic Gene Therapy by Mutation-Specific E-cadherin Antibodies possible ways for a specific gene transfer:
  coupling to viral gene expression systems (e.g. adenovirus, or MVA, vaccinia-derived expression vectors);
  coupling to non-viral gene expression systems (e.g. T7 RNA polymerase+T7 DNA vector);
Possible therapy approach using genetic engineering:
  incorporation of cofactors (e.g. B7) to label the tumor cells for the endogenous immune system;
  incorporation of alloantigens (foreign HLA antigens, "major antigens") to activate the endogenous T cells and initiate an immune reaction against tumor cells having mutated E-cadherin "minor antigen");
  killing of tumor cells by specific incorporation of factors inducing apoptosis (e.g. p53); conversion of the malignant phenotype by specific incorporation of wildtype oncogenes/suppressor genes (e.g. E-cadherin itself); activation of a protoxin to form a toxin by specific inclusion of an enzyme (e.g. cytosin deaminase, conversion of 5-fluoro cytosin into the toxic 5-fluoro uracil);

Ribozymes e.g. site-specific destruction of the RNA coding for the multidrug-resistance transporter Further Examples Showing Fields of Use of the E-cadherin Mutations bone marrow purging:
  specific determination of tumor cells in treated bone marrow in vitro and concurrent use of the antibody for specific elimination of tumor cells from the bone marrow (e.g. by a toxin bound to the antibody);
immune therapy
  charging of dendritic cells with mutated E-cadherin peptide sequences (see Table 3) for antigen presentation (activation of T cell clones specifically directed against tumor cells).

The intracellular degeneration of proteins generates peptides having different lengths. Peptides with a length of 9–11 amino acids are "checked" by the MHC of the cell (the binding capacity in the peptide binding region depends on a particular arrangement of the individual amino acids and distinguishes between "nonself" and "self") and are presented at the cell surface if a particular sequence has been recognized as nonself. By the action of costimulators, this can lead to an immune reaction. For the peptide sequences of the mutated E-cadherin described for the first time by us and other peptides being generated by mutations, it can be expected that some of them will be presented by the MHC as nonself peptides. The fact that this event fails to stimulate an immune reaction in patients may be explained by the property of tumor cells to present antigens poorly. The mutation-spanning peptides found can be mounted—in varying lengths—on professional, antigen presenting cells (dendritic cells). Due to the presence of all neccessary costimulators on this cells a corresponding T cell stimulation against such MHC-peptide complexes is achieved. In this way, also the tumor cells which initially have been ignored by the immune system are then recognized as nonself and are eliminated.

This use does not require a particular mutation-specific antibody, however, it requires knowledge about the newly generated peptide sequences described according to the invention.

According to the invention, also the following objects and methods are comprised:
monoclonal antibody specifically directed against such amino acid sequences of mutated E-cadherin which have been generated by in-frame mutations on the DNA level and a. lead to the loss of at least one base triplet or a multimer thereof in an exon on the RNA level and subsequently lead to the deletion of at least one amino acid of the wt E-cadherin protein, and/or b. lead to the exchange of one or two nucleotides of at least one base triplet in an exon on the RNA level and subsequently to the exchange of at least one amino acid of the wt E-cadherin protein.

Monoclonal antibody directed against such sequences of mutated E-cadherin which have been generated by in-frame mutations on the DNA level and lead to the loss of at least one base triplet or a multimer thereof in exon 8, exon 9, or exon 10 on the RNA level.

Monoclonal antibody recognizing at least the sequence region among one or more of the following amino acid sequences which has been generated by deletion or amino acid exchange as compared to E-cadherin, selected from at least one sequence of the following group:

| Mutation | Mutated E-cadherin sequence | SEQ ID NO: |
|---|---|---|
| 563del63 | PGLRRQKRDW/IKSNKDKEGK | SEQ ID NO:2 |
| 706del9 | QGADTPPVGV/ERETGWLKVT | SEQ ID NO:4 |
| 1036del15 | LSQDPELPDK/NRNTGVISVV | SEQ ID NO:6 |
| 1103del129 | SVVTTGLDRE/YKGQVPENEA | SEQ ID NO:8 |
| 1232del183 | DNPPIFNPTT/GLDFEAKQQY | SEQ ID NO:10 |

Mutated E-cadherin sequence

| Mutation | Mutated E-cadherin sequence | SEQ ID NO: |
|---|---|---|
| 1414del69 | NNDGILKTAK/VSLTTSTATV | SEQ ID NO:12 |
| Asp370Ala | TAVITVTDTNANPPIFNPTT | SEQ ID NO:14 |
| Val473Asp | EVSLTTSTATDTVDVLDVNE | SEQ ID NO:16 |
| Arg598Gln | VNDNAPIPEPQTIFFCERNP | SEQ ID NO:18 |
| 826del9 | AVSSNGNAVEE/ILITVTDQN | SEQ ID NO:20 | wherein "/" denotes the position of a deletion, and bold letters denote amino acids changed by point mutations, respectively, each in comparison to the wild-type E-cadherin protein.

The invention also comprises a mixture of at least two of the above mentioned monoclonal antibodies.

The invention comprises in particular monoclonal antibodies as those described above which are specifically directed against the amino acid sequences of mutated transmembrane E-cadherin.

A further embodiment of the invention comprises an immune test for the detection of gastric carcinoma cells comprising at least one monoclonal antibody of the present invention.

Furthermore, the invention comprises the following embodiments:

Primers for PCR processes for the amplification of DNA and cDNA sequences of mutated exon regions of E-cadherin selected to specifically comprise the mutated sequences generated by in-frame mutations on the DNA level which a. lead to the loss of at least one base triplet or a multimer thereof in an exon on the RNA level and subsequently lead to the deletion of at least one amino acid of the wt E-cadherin protein, and/or b. lead to the exchange of one or two nucleotides of at least one base triplet in an exon on the RNA level and subsequently to the exchange of at least one amino acid of the wt E-cadherin protein.

Primers for PCR processes for the amplification of DNA and cDNA sequences of mutated exon regions of E-cadherin selected to specifically comprise the mutated sequences and selected from at least one primer of the following group:

| Primer name | Sequence | |
|---|---|---|
| ATG | 5'-ATGGGCCCTT GGAGCCG | (SEQ ID NO:21) |
| Ex 8 | 5'-CTACGTATACC CTGGTGG | (SEQ ID NO:22) |
| Ex 9/1 | 5'-TACAAGGGTC AGGTGCCTGAG | (SEQ ID NO:23) |
| rEx 10 | 5'-GGGGGCTTCAT TCACATC | (SEQ ID NO:24) |
| r3'/2/ neu | 5'-CCAGCACATG GGTCTGGG | (SEQ ID NO:25) |
| Ex 7 | 5'-ACCTCTGTGAT GGAGGTC | (SEQ ID NO:26) |
| rEx 11 | 5'-TGTGTACGTGC TGTTCTTCACGTG | (SEQ ID NO:27) |

| Name and sequence of the ~forward primer | Name and sequence of the "reverse" primer |
|---|---|
| ATG; 5-CCATGCGCCCT TGGAGCCGC (SEQ ID NO:28) | rEx 6; 5'-CTGGAAGAGCA CCTTCCATGAC (SEQ ID NO:29) |
| Ex 5; 5'-ACAGAGCCTCTG GATAGAGAACGC (SEQ ID NO:30) | rEx 10/2; 5'-CCACATTCGT CACTGCTACG (SEQ ID NO:31) |
| Ex 9/2a 5'-CAGCGTGGGA GGCTGTATACAC (SEQ ID NO:32) | rEx 11; 5'-TGTGTACGTGC TGTTCTTCAC (SEQ ID NO:33) |
| Ex 10/2; 5'-GTGTCCGAGG ACTTTGGCGTG (SEQ ID NO:34) | rEx 13; 5'-TCAGAATTAGC AAAGCAAGAATTCC (SEQ ID NO:35) |
| Ex 13; 5'-GGCGTCTGTAG GAAGGCACAG (SEQ ID NO:36) | r3prime; 5'-CCAGCACATG GGTCTGGG (SEQ ID NO:37) |

It is particularly preferred that the invention comprises therapeutic or diagnostic means containing as an effective substance at least one nucleic acid which specifically hybridizes to the DNA or cDNA or to RNA sequences derived therefrom of mutated E-cadherin wherein the DNA or cDNA exhibits in-frame mutations which a. lead to the loss of at least one base triplet or a multimer thereof in an exon on the RNA level and subsequently lead to the deletion of at least one amino acid of the wt E-cadherin protein, and/or b. lead to the exchange of one or two nucleotides of at least one base triplet in an exon on the RNA level and subsequently to the exchange of at least one amino acid of the wt E-cadherin protein.

Furthermore, the invention comprises therapeutic or diagnostic means containing a nucleic acid which hybridizes to at least some of the following DNA sequences or complementary strands thereof or RNA sequences derived therefrom under stringent conditions wherein also at least the sequence region generated by in-frame mutation is included:

Mutation 563del63:

CCT GGC CTC AGA AGA CAG AAG AGA GAC TGG/
ATC AAA TCC AAC AAA GAC AAA GAA GGC AAG
(SEQ ID NO:38)

Mutation 706de19:

CAA GGA GCT GAC ACA CCCCCT GTT GGT GT/T
GAA AGA GAA ACA GGA TGG CTG AAG GTG ACA
(SEQ ID NO:39)

Mutation 1036de115:

CTC AGC CAA GAT CCT GAG CTC CCT GAC AAA/
AAC AGG AAC ACA GGA GTC ATC AGT GTG GTC
(SEQ ID NO:40)

Mutation 1103delde1129:

AGT GTG GTC ACC ACT GGG CTG GAC CGA GAG/
TAC AAG GGT CAG GTG CCT GAG AAC GAG GCT
(SEQ ID NO:41)

Mutation 1232de1183:

GAT AAT CCT CCG ATC TTC AAT CCC ACC ACG/GGC TTG GAT TTT GAG GCC AAG CAG CAG TAC (SEQ ID NO:42)

Mutation 1414de169:

AAC AAC GAT GGC ATT TTG AAA ACA GCA AAG/ TCT CTC ACC ACC TCC ACA GCC ACC GTC (SEQ ID NO:43)

Mutation Asp370Ala:

ACA GCT GTG ATC ACA GTC ACT GAC ACC AAC GCT AAT CCT CCG ATC TTC AAT CCC ACC ACG (SEQ ID NO:44)

Mutation Val473Asp:

GAG GTC TCT CTC ACC ACC TCC ACA GCC ACC GAC ACC GTG GAT GTG CTG GAT GTG AAT GAA (SEQ ID NO:45)

Mutation Arg598Gln:

GTG AAT GAC AAC GCC CCC ATA CCA GAA CCT CAA ACT ATA TTC TTC TGT GAG AGG AAT CCA (SEQ ID NO:46)

Mutation 826de19:

GCT GTG TCA TCC AAC GGG AAT GCA GTT GAG GA/G ATT TTG ATC ACG GTA ACC GAT CAG AAT (SEQ ID NO:47)

Moreover, according to the invention there are also comprised therapeutic or diagnostic means containing as an effective substance a nucleic acid which hybridizes to the above mentioned nucleic acid under stringent conditions.

Stringent conditions in the spirit of the present invention are defined as conditions which allow for selective and detectable specific binding of the nucleic acid to the nucleic acid defined according to the invention. A hybridisation of this kind under stringent conditions preferably means a hybridisation carried out at 68° C. in aqueous solution comprising 5×SSC or at 42° C. in 50% formamide solution comprising 5×SSC and subsequent washing of the filter at a temperature of 65° C. in an aqueous solution comprising 0.2×SSC after which binding of the probe to the nucleic acid defined according to the invention or to the RNA derived therefrom can still be detected. If neccessary, also less severe hybridisation and/or washing conditions may be used.

The monoclonal antibodies provided according to the invention are useful in diagnosis and therapy of gastric carcinomas and in particular of diffuse gastric carcinoma.

For therapy, the monoclonal antibodies of the invention may for example be bound to a means for selective elimination of at least some of the gastric carcinoma cells. This means may preferably include a toxin or a source of radiation.

According to preferred embodiments of the invention, the source of radiation is a β-emitting radionuclide, preferably $^{131}$I, $^{188}$Re or $^{90}$Y. By choosing the appropriate radionuclide, the range of the cytotoxic effect can be matched to the size of the tumor. For example, for the radioimmunotherapy of malignancies with large tumor masses, β-emitting radionuclides such $^{131}$I, $^{188}$Re or $^{90}$Y, with mean tissue ranges of 0.9 to 3.9 mm, are preferably coupled to the monoclonal antibodies of the present invention.

For selective irradiation of single tumor cells or small tumor cell clusters, the approach of labeling tumor-specific monoclonal antibodies of the present invention with α-emitting nuclides is preferred. The α-particels emitted by $^{212}$Bi, $^{211}$At or $^{213}$Bi have short ranges of only 50–100 $\mu$m and a high LET of ~100 keV/$\mu$m that deposit a large amount of energy within a few cell diameters.

As a toxin, which is coupled to the monoclonal antibody of the present invention, a toxin can be used which is selected from, for example, Pseudomonas exotoxin, Ricin, DM1, Doxorubicin.

The present invention also comprises the DNA oligonucleotides and the oligopeptides characterized in more detail in the claims. These are useful for immunotherapy of tumors, especially of gastric carcinomas.

In a further embodiment of the invention, there is described a process for the determination of tumor cells in a sample material containing human cells by the following steps of:

a. providing sample material containing human cells;

b. recovery of the mRNA from the human cells;

c. reverse transcription of the mRNA;

d. performing a polymerase chain reaction using the primers according to claims 8 or 9;

e. separating and analyzing the reaction products of the polymerase chain reaction.

The invention further comprises a method for the detection of diffuse gastric carcinoma, comprising the steps of:

a) providing at least one of the monoclonal antibodies of the invention, which are coupled to detectable means, b) contacting said at least one detectable monoclonal antibody with cells or tissues which are suspected to be diffuse gastric cancer cells/tissues, and c) determining the amount of the at least one detectable monoclonal antibody bound to said cells or tissues.

The present invention further provides the above-described antibodies in detectably labeled form (labeled by detectable means). Antibodies can be detectably labeled through the use of detectable means such as radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art, for example, see Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goading J. W. J:Immunol. Meth. 13:215 (1976). The labeled antibodies of the present invention can be used for in vitro, in vivo, and in situ assays to identify cells or tissues in which mutant E-cadherin sequences are expressed.

Also provided is a method for treating diffuse gastric carcinoma in an animal, comprising: administering to an animal in need of such treatment, a monoclonal antibody of the present invention, preferably coupled to a means for the slective elimination of at least some of the gastric carcinoma cells in a dosage effective to substantially eliminate the diffuse gastric carcinoma in said animal.

However, it might be recommendable to perform a detection step prior to the treatment step for the following reasons: A rat MAb, designated d9MAb, which is disclosed below, specifically reacts with mutant E-cadherin lacking exon 9 but not with the wild-type protein. This monoclonal antibody, which is similar to the herein disclosed MAb 7E6, also recognizes the mutant E-cadherin amino acid sequence of SEQ ID NO 10, i.e. the sequence with complete loss of exon 9. This MAb was found to react with 13% of E-cadherin-expressing diffuse-type gastric cancers. Therefore, it is preferred to choose a two-step approach, wherein at first a detection step is performed, in order to detect a diffuse gastric carcinoma, which expresses the inventive mutant E-cadherin sequences, and, at second, the treatment with the herein disclosed Mab's is performed.

Thus, according to a preferred embodiment, a method of treating diffuse gastric carcinoma in an animal comprises the following steps:

a) determining the absence or presence of a diffuse gastric cancer which expresses any one of the mutated E-cadherin sequences of SEQ ID NO: 2, 4, 6, 8, 10, 12, 16, 18 or 20, by the above mentioned detection method, and, in case of presence, b) treating the animal in accordance with the above mentioned treating method.

The animal preferably is a mammal and more preferably a human being.

The invention also comprises vectors containing the oligonucleotide sequences provided according to the invention.

Thus, it has been discovered by the invention that in-frame mutations of E-cadherin may be used in diagnosis and therapy of gastric carcinomas. The term "in-frame mutations" is intended to mean mutations or deletions in E-cadherin taking place on the DNA level which lead to a deletion or an base exchange on the RNA level while neither the deletion nor the mutation leads to a reading frame displacement.

EXAMPLES

Methodology

1. Search for New E-cadherin Mutations

Tissue of 63 patients suffering from gastric carcinoma was examined. Fresh tumor tissue after resection was deep-frozen in liquid nitrogen. Total RNA of the deep-frozen tissue samples was isolated using standard procedures (guanidinium isothiocyanate extraction and CsCl centrifugation). Following reverse transcription of two µg of RNA the whole coding region of the E-cadherin cDNA was amplified by PCR. The PCR primers used are listed in Table 4. The amplification conditions for all of the PCR reactions were as follows: 1 min denaturation at 94° C.; 1 min primer annealing at 55° C.; and 1 min elongation at 72° C. Taq polymerase and amplification buffer (1.5 mM $MgCl_2$) were obtained from Perkin Elmer Corp., Foster City, Calif., USA. A Biomed PCR device (Biomed-Labordiagnostik, Oberschleiβheim) was used. The products of the amplification were checked by agarose gel electrophoresis, and were subsequently purified using glass milk (GeneClean II, Bio101 Inc., La Jolla, Calif., USA). Afterwards, the full lengths of the isolated DNA amplificates were sequenced (Sequenase Version 2.0/USB, Cleveland, Ohio, USA).

TABLE 4

E-cadherin cDNA primers for PCR amplification of the complete coding sequence.

| Name and sequence of the "forward" primer | Name and sequence of the "reverse" primer | Nucleotide position* and length of the PCR product |
|---|---|---|
| ATG; 5'-CCATGGGCCCT TGGAGCCGC (SEQ ID NO:28) | rEx 6; 5'-CTGGAAGAGCA CCTTCCATGAC (SEQ ID NO:29) | 93–926; 834 bp |
| Ex 5; 5'-ACAGAGCCTCTG GATAGAGAACG (SEQ ID NO:30) | rEx 10/2; 5'-CCACATTCGT CACTGCTACG (SEQ ID NO:31) | 743–1472; 730 bp |
| Ex 9/2a; 5'-CAGCGTGGGA GGCTGTATACAC (SEQ ID NO:32) | rEx 11; 5'-TGTGTACGTGC TGTTCTTCAC (SEQ ID NO:33) | 1314–1780; 467 bp |
| Ex 10/2; 5' GTGTCCGAGG ACTTTGGCGTG (SEQ ID NO:34) | rEx 13; 5'-TCAGAATTAGC AAAG-CAAGAATTCC (SEQ ID NO:35) | 1577–2264; 688 bp |
| Ex 13; 5'-GGCGTCTGTAG GAAGGCACAG (SEQ ID NO:36) | r2prime; 5'-CCAGCACATG GGTCTGGG (SEQ ID NO:37) | 2171–2781; 611 bp |

*With respect to the E-cadherin sequence Z13009 in the EMEL/GenBank sequence data banks. (The translated region extends from nucleotide 95–2743)

2. Immunohistochemical Examination (Not Mutation-Specific)

Archive material of tissue fixed in formalin and embedded in paraffin was subjected to deparaffinization and rehydration. Following treatment with citric acid and microwaves, the tissue samples were incubated for 15 minutes in 1% $H_2O_2$ to block endogenous peroxidase. For the determination of E-cadherin-specific immunoreactivity the tissues were incubated for 16 hours at 4° C. with the monoclonal antibody HECD-1 (Takara Biomedicals, Japan, 1:500 dilution). Visualisation of antibody binding was carried out using the avidin-biotin complex (ABC) and the peroxidase method (ABC Elite Kit, Vector, Burlingame, Calif.; Sigma Fast DAB, Sigma, Deisenhofen). Hemalum was used for counterstaining of the nucleus. All of the tumor sections also showed portions of non-malignant mucosa as a control. Negative controls were performed by substituting the HECD-1 antibody by phosphate-buffered NaCl.

3. Cloning of E-cadherin into Expression Vectors

To examinate the intracellular localisation of mutated E-cadherin the mutated molecules were cloned into expression vectors. As an example, 4 different mutants of E-cadherin mRNA in addition to human wild-type E-cadherin were cloned into expression vectors. Two of these 4 mutations exhibited a complete loss of one of the exons, either a deletion of exon 8 (129 bp) or a deletion of exon 9 (183 bp). Another mutation shows a partial deletion of exon 10 (63 bp). The fourth mutation consists of a base exchange in exon 8 which disrupts a potential calcium binding site. All of the mutations considered for expression cloning are in the extracellular region of E-cadherin (see FIG. 1 for all mutations).

Starting material for cloning was total RNA isolated from fresh material of diffuse gastric carcinomas in which a respective mutation (see above) was identified. Each of the cDNAs of wild-type E-cadherin and of the mutations obtained after reverse transcription were amplified in the form of two partial fragments (A+B) (see FIG. 7). Taken together, the two partial fragments comprise the complete coding region of E-cadherin consisting of 2649 bp (wild-type). The amplification of fragment A (5' region) was performed using primers ATG and rEX10 (see Table 5). For the amplification of the 3' fragment (B) of the wild-type mRNA, the exon 9 deletion, the partial deletion in exon 10, and the point mutation in exon 8 the pair of primers Ex8-r3'/2/neu was employed. Amplification of fragment B' of the exon 8 deletion mutant was done using the pair Ex 9/1-r3'/2/neu.

The partial fragments A and B amplified were each cloned into PCRII vectors (Invitrogen). Using these vectors a direct and effective cloning of PCR products by means of specific TA base pairing can be achieved. The two partial cDNA fragments of all 5 cadherin cDNAs (wild-type plus 4 mutants) were appropriately joined together by cloning using different cloning strategies which will not be detailed herein but which are well within the skill and the knowledge of one skilled in the art. In this way, constructs of all 5 cDNA in PCRII vectors were obtained.

To exclude cloning artefacts which could have been generated mainly in the course of the amplification (Taq mistakes) all of the 5 cDNAs were examined by sequencing of their full lengths including the vector/cadherin junction regions.

TABLE 5

PCR primers for amplification of E-cadherin and subsequent cloning

| Primer Name | Sequence | Position in E-cadherin mRNA* |
| --- | --- | --- |
| ATG | 5'-ATGGGCCCTT GGAGCCG (SEQ ID NO:21) | 95–111 |
| Ex 8 | 5'-CTACGTATACC CTGGTGG (SEQ ID NO:22) | 1110–1128 |
| Ex 9/1 | 5'-TACAAGGGTC AGGTGCCTGAG (SEQ ID NO:23) | 1232–1252 |

TABLE 5-continued

PCR primers for amplification of E-cadherin and subsequent cloning

| Primer Name | Sequence | Position in E-cadherin mRNA* |
| --- | --- | --- |
| rEx 10 | 5'-GGGGGCTTCAT TCACATC (SEQ ID NO:24) | 1529–1546 |
| r3'/2/neu | 5'-CCAGCACATG GGTCTGGG (SEQ ID NO:25) | 2764–2781 |
| Ex 7 | 5'-ACCTCTGTGAT GGAGGTC (SEQ ID NO:26) | 929–946 |
| rEx 11 | 5'-TGTGTACGTGC TGTTCTTCACGTG (SEQ ID NO:27) | 1757–1780 |

*With respect to the E-cadherin sequence Z13009 in the EMEL/GenBank sequence data banks. (The translated region extends from nucleotide 95–2743)

In a further step the cadherin constructs verified by sequencing were cloned into eukaryotic expression vectors. On the one hand, the commercially available vector PBK-CMV (Stratagene) which allows for selection of the expressed cellular clones (expression of the neomycin resistance gene) in addition to the expression of the desired cDNA was chosen, on the other hand as a second vector the pBAT vector was used which has already been employed successfully in the transfection of murine wild-type E-cadherin constructs (Nose, A, Nagafuchi, A, Takeichi, M. Expressed recombinant cadherins mediate cell sorting in model systems. Cell 1988; 54:993–1001).

4. Transient Transfection and Detection of E-cadherin by Western-blotting, Immunofluorescence and Immunoelectron Microscopy The $CaPO_4$ precipitation was established for transfection. The transfection efficiency of the method was evaluated using a pCMV plamid (Stratagene) as a control. The vector contains the β-galactosidase gene which allows for detection of the cells having incorporated the vector after conversion of the dye X-Gal (blue stain). The efficiency of the method was in the range of 10% which is a very good value for transient transfections.

In the expression experiments following amplification of the 5' untranslated region which contains the translation recognition region (Kozak sequence) and cloning thereof upstream of the cDNAs it was possible to express the E-cadherin cDNA constructs altered in that manner transiently in MDA-MB-435S cells, MIA PaCa-2, a pancreas cell line deficient for E-cadherin, and in Neuro 2A (neuroblastoma) cells.

The determination of E-cadherin in the cell cultures was done by Western-blotting, immunofluorescence, and immunoelectron microscopy. At first, SDS lysis of the cells (transfected or untransfected) was performed to prepare a whole cell lysate for Western-blotting. Doing this, we obtained an irregular electrophoretic mobility during the subsequent gel run which is neccessary for the examination of the lysate. Alternatively, a cellular extract by Triton X-100 lysis was tested. Examination of the extract by polyacrylamide gel electrophoresis and Coomassie staining showed the disruption of the cells to be effective. Therefore, Triton lysis was used for all subsequent experiments.

We used 4 different monoclonal antibodies against E-cadherin (HECD-1, Takara Biomedicals, Japan; AMST10, Saxon Biomedicals; DECMA-1, Sigma; ANTI-E-

CADHERIN, Affinity Research Products Limited) for the specific determination of E-cadherin. The detection of the antigen-antibody complex during Western-blotting was done by a luminescence reaction (ECL-Western, Amersham) using a second peroxidase labeled antibody. Although they reacted with different intensities, all of the antibodies tested showed a specific reaction in the cellular extract with an E-cadherin positive control cell line, A431 (epidermoid carcinoma, ATCC), and with MDA-MB-435S cells transfected by wild-type E-cadherin. No positive signal could be detected in the extracts of the untransfected lines MDA-MB-435S, MIA PaCa-2 and Neuro 2A.

To perform the immunofluorescence, cells seeded onto cover slips were fixed by methanol and labeled by the antibody HECD-1 specific for E-cadherin (recognizes wild-type E-cadherin and mutated, e.g. exon 9 deleted E-cadherin). As a secondary antibody rhodamine-(TRITC-) coupled goat-anti-mouse antibodies (Dianova) were employed.

To determine by means of immunofluorescence whether the transfection had been successful, non-transfected MDA-MB-435S cells, and cells transfected by mutated E-cadherin and by wild-type E-cadherin were examined concurrently. After fixation and incubation with gold-labeled antibody specific for E-cadherin (HECD-1) the labeled cells were embedded in epon and contrasted by uranyl acetate/lead citrate. No labeling could be detected with untransfected MDA-MB-435S cells while the transfected cell lines showed gold labeling associated with the membranes, i.e. wild-type E-cadherin as well as mutated E-cadherin (e.g. having an exon 9 deletion, see FIG. 3) were anchored in the membrane.

5. Cell Lines Stably Expressing E-cadherin

After we were successful in identifying wild-type as well as mutated E-cadherin in transiently transfected cells we started with the preparation of cells stably expressing E-cadherin. This was performed by cotransfection of MDA-MB-435S cells with the respective pBAT constructions (see "Cloning") and with pBAT vector without E-cadherin cDNA but instead including the neomycin resistance gene. Three cell lines exhibiting a deletion in exon 9 (Del 9) of the human E-cadherin gene and three lines harbouring the wild-type human E-cadherin (WT) were established. Examination of the mRNA by RT-PCR of the Del-9 lines and the WT lines showed the expected fragment sizes (mRNA of normal size for the wild-type (779 bp); shortened mRNA for the Del-9 lines (596 bp), in this case, no wild-type E-cadherin mRNA was expressed!) PCR amplification was carried out using the primers Ex7 and rEX11 (see Table 5). The Western blot of extracts of stably transfected Del-9 lines and of one of the WT lines clearly detected E-cadherin protein.

Figure 2:
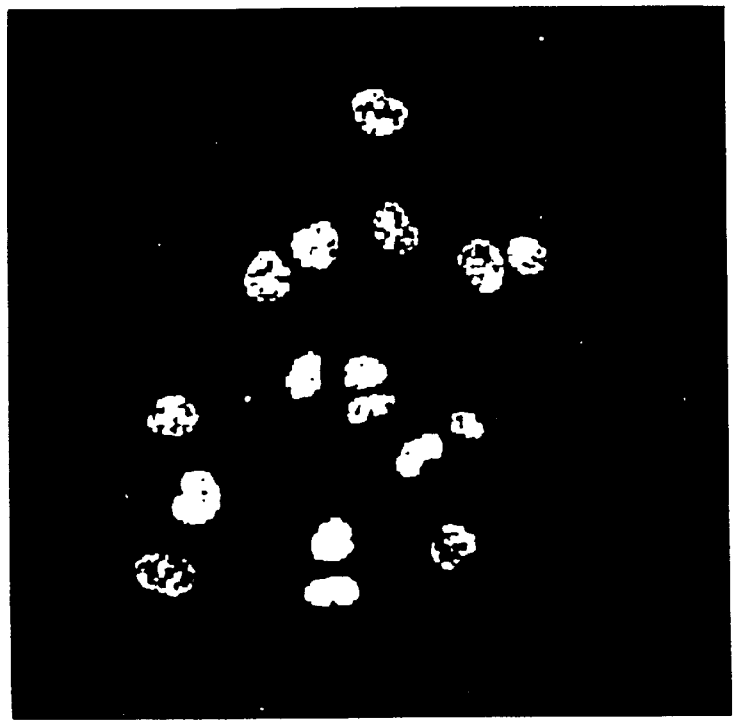
FIG. 2. The determination of the membraneous localisation of mutated E-cadherin by immunofluorescence.
Figure 3:
FIG. 3. The determination of the membraneous localisation of mutated E-cadherin by immunoelectron microscopy.

Examination of the E-cadherin expression in the WT line using immunofluorescence revealed the expected characteristic distribution at the contact sites to the neighbour cell. Using the HECD-1 antibody, the Del-9 cell line also showed labeling of E-cadherin at the cell-to-cell junctions (FIG. 2).

6. Rapid RNA Extraction and Subsequent Determination of the Mutations by PCR (Using Peritoneal Lavage as an Example)

Following sedimentation of the cells in the lavage preparation and RNA extraction (Rneasy Rapid extraction Kit, Quiagen) the RNA is reverse transcribed and the full length of the resulting E-cadherin cDNA is amplified by means of PCR (primers and conditions as above). Since the E-cadherin mutations consist mainly of in-frame deletions, these may be quickly and safely detected by agarose gel electropheresis. Thus, already 9 hours after receiving the lavage there may be detected possible deletions in E-cadherin, e.g. loss of exon 8 or exon 9, and thereby the detection of disseminated tumor cells in the peritoneal cavity is possible. Due to this information the course of clinical decisions may be directly affected (e.g. additional intraperitoneal therapies).

By this, a highly specific method of detection can be performed rapidly and safely—and also with a low amount of tumor cells. The tumor specificity of the E-cadherin mutations make it possible to exclude ambiguities with respect to cells with "tumor-like" morphology, such as inflammatory mesothelial cell.

7. Preparation and Testing of a Mutation-Specific E-cadherin Antibody (Using Antibody 7E6 Specific for the Exon 9 Deletion as an Example)

Peptide synthesis. The following peptide was prepared using a model 430A peptide synthesizer (Applied Biosystems, Foster City, Calif., adapted to Fast-Fmoc modification) (peptide sequence: E-cadherin deletion of exon 9, see Tab. 3 1232del183): Pro-Ile-Phe-Asn-Pro-Thr-Thr-Gly-Leu-Asp-Phe-Glu-Ala (SEQ ID NO:48). The amino acids Asn, Thr, Asp, and Glu were synthesized with protected side chains. The peptide was released off the synthesis resin in 95% trifluoroacetic acid, precipitated by tert butylether and freeze-dried. Afterwards, the raw product was dissolved in 0,1% trifluoroacetic acid and purified using a reverse phase column (Aquapore 300A, C8, Applied Biosystems) with a linear gradient in 70% acetonitrile. The purity of the product was tested in a model AP100 mass spectrometer (Perkin Elmer) by electric spray ionisation.

Coupling to a carrier and immunisation: keyhole limpet hemocyanin (KLH) from Megathura crenulata (Calbiochem, Bad Soden) was used as a carrier protein for the immunisation and was coupled to the peptide in 0.5 M N-methylimidazole buffer (Sigma-Aldrich, Steinheim) pH 7.0 using 1-ethyl-3-(dimethylamino-propyl)carbodiimide at room temperature. In total, 2.8 mg of the peptide were coupled to 2.0 mg of hemocyanin. After dialysis against phosphate-buffered saline (PBS) the resulting solution was used for immunization. The same method was used for the coupling of 2 mg of the peptide to 2 mg of 4×crystallized bovine serum albumine (Behringwerke, Marburg) which was used to test the hybridoma culture supernatants in the ELISA test. The immunisation was performed in Lou/C rats, and 50 µg of KLH-coupled peptide were diluted using 500 µl PBS and were emulsified by the same amount of CFA. 500 µl of the resulting emulsion were applied i.p. and s.c., respectively. Three months later a boost injection was performed using KLH-coupled peptide but without CFA. The fusion was carried out 3 days after boost injection. The murine plasmocytoma cell line P3×63 Ag 8.653 served as fusion cell line. An ELISA was performed to test for the specific peptide and for an irrelevant peptide coupled to BSA using identical coupling chemistry which served as a control. Hybridomas reacting exclusively with the specific peptide were frozen, and the supernatants thereof were subjected to further analysis. Subclasses were determined using subclass-specific monoclonal antibodies.

FACS analysis: 200.000 MDA-MB-435S cells transfected with exon 9 deleted E-cadherin (see above) or 200.000 untransfected MDA-MB-435S cells, respectively, were incubated together with 50 µl of hybridoma supernatant. 50 µl of suitably diluted goat-anti-rat FITC were added for 30 min to detect the bound antibodies. The cells were analysed in the FACscan (Becton). The mab 7E6 belongs to the "rat IgG1" subclass and shows the highest intensity in the FACscan.

Immunofluorescence: To perform the immunofluorescence, the cells seeded on cover slips (MDA-MB-435S cells transfected by exon 9 deleted E-cadherin or untransfected MDA-MB-435S cells, respectively) were fixed with methanol and labeled by antibody 7E6 specific for E-cadherin mutations. As a secondary antibody, FITC-coupled goat-anti-rat antibody (Dianova) was used.

Western-blotting: Cellular extracts of E-cadherin transfected MDA-MB-435S cells (transfected either with wild-type or exon 9 deleted E-cadherin) and of additional cell lines were examined by the mutation-specific antibody 7E6 on a Western blot. Using the antibody 7E6 no positive signal could be detected in the extracts of the untransfected lines MDA-MB-435S, MIA PaCa-2 (human pancreatic carcinoma), Neuro 2A, and A431 (epidermoid carcinoma, ATCC). Also, the cells transfected by wild-type E-cadherin failed to show a signal with 7E6. The only cell line which had reacted with the mutation-specific E-cadherin antibody 7E6 was MDA-MB-435S which had been transfected by exon 9 deleted E-cadherin.

Immunohistochemistry: Archive marterial (formalin-fixed and paraffin-embedded tissue) of gastric carcinoma patients in which the loss of exon 9 of E-cadherin had been detected by molecular biology was subjected to deparaffinization and rehydration. After treatment with citric acid and microwaves the tissue samples were incubated for 15 minutes in 1% $H_2O_2$ to block the endogenous peroxidase. For the detection of E-cadherin mutation-specific immunoreactivity the tissues were incubated with 7E6 monoclonal antibody at 4° C. over 16 hours. Binding of the antibody was visualized using avidin-biotin complex (ABC) and the peroxidase method (ABC Elite Kit, Vector, Burlingame, Calif.; Sigma Fast DAB, Sigma, Deisenhofen). Counterstaining of the nucleus was performed using hemalum. All of the tumor sections also showed portions of non-malignant mucosa as a control. Negative controls were carried out substituting the 7E6 antibody by phosphate-buffered NaCl.

8. Preparing and Testing Radio-Labeled Conjugates of d9Mab, Which was Coupled to Several Radionuclides, in the Detection and Therapy of Diffuse Gastric Carcinoma A monoclonal antibody (E-cadherin delta 9-1) directed against a characteristic E-cadherin mutation (in-frame deletion of exon 9, corresponding to SEQ ID NO:10), found in diffuse-type gastric cancer but not in any normal tissue, was conjugated with the high linear energy transfer α-emitter $^{213}$Bi and tested for its binding specificity in s.c. and i.p. nude mice tumor models. After intra-tumoral application in s.c. tumors expressing mutant E-cadherin, the $^{213}$Bi-labeled antibody was specifically retained at the injection site as shown by autoradiography. After injection into the peritoneal cavity, uptake in small i.p. tumor nodules expressing mutant E-cadherin was 17-fold higher than in tumor nodules expressing wild-type E-cadherin (62% injected dose/g versus 3.7% injected dose/g). 78% of the total activity in the ascites fluid was bound to free tumor cells expressing mutant E-cadherin, whereas in control cells, binding was only 18%. The selective binding of the $^{213}$Bi-labeled, mutation-specific monoclonal antibody E-cadherin d 9-1 suggests that it will be successful for a-radioimmunotherapy of disseminated tumors after locoregional application.

A rat MAb, designated d9MAb, was generated that specifically reacts with mutant E-cadherin lacking exon 9 but not with the wild-type protein. d9Mab was found to react with 13% (22 of 172) of E-cadherin-expressing diffuse-type gastric cancers (6). Because of this specific tumor cell targeting, d9MAb coupled with the α-emitting radionuclide $^{213}$Bi could have a significant potential for the locoregional radioimmuno-therapy of disseminated, diffuse-type gastric carcinoma, which is often associated with i.p. spread of single malignant cells leading to peritoneal carcinomatosis. The advantages of α-particles are their high LET and their short range of a few cell diameters. These features result in a high localized energy deposition, even in single target cells, and minimal irradiation of surrounding normal tissue. We have established an i.p. tumor model using cells expressing E-cadherin with an exon 9 deletion that mimics the clinical situation in human gastric cancer with i.p. tumor spread that is known to be a crucial process in diffuse-type gastric cancer. The free i.p. application of a tumor-specific MAb labeled with an appropriate radionuclide seems to be an effective treatment of peritoneal tumor spread. Here we report that the d9MAb coupled with the α-emitter $^{213}$Bi specifically binds to mutant E-cadherin after locoregional application.

Antibody

The rat MAb recognizing mutant E-cadherin lacking exon 9 was generated as described previously (6). Briefly, a 13-amino acid peptide spanning the fusion junction between exons 8 and 10 of mutant E-cadherin with an exon 9 deletion was injected into Lou/C rats i.p. and s.c. for immunization. After fusion of the immune rat spleen cells with a myeloma cell line, hybridoma supernatants were tested by a solid phase immunoassay using the mutation-specific peptide coupled to BSA. A tumor cell-specific, MAb against the delta 9 peptide, referred to as d9MAb (clone 6H8) was selected for the studies described below.

Conjugation of Chelate to d9MAb and Radiolabeling d9MAb was conjugated to SCN-CHX-A0-DTPA as described previously (7, 8). The number of chelates per antibody ranged from 5 to 10 as determined by a standard $^{111}$In-assay (9). For comparative binding studies, both the MAb chelate construct and the MAb without chelate were labeled with $^{125}$I according to the Iodogene method. $^{213}$Bi (t ½=46 min) was eluted from a $^{225}$Ac/$^{213}$Bi generator provided by the Institute for Transuranium Elements, Karlsruhe, Germany (10), with 0.1 M HCl/0.1 M NaI as the $BiI_4^-$/$BiI_5^{2-}$ anion. The eluant was adjusted to pH 5.3 with 2 M ammonium acetate, and ~100 µg of the chelated antibody were added and allowed to react for 5 min. The $^{213}$Bi-immunoconjugate was purified by size exclusion chromatography (Pharmacia PD-10) with 2 ml of PBS.

The coupling of $^{111}$In (InCl$_3$, Mallinckrodt) to the chelated d9MAb was carried out using the $^{213}$Bi-protocol omitting NaI. The $^{111}$In-immunoconjugate was applied for scintigraphic imaging of i.p. retention and biodistribution. The labeling efficiency was assayed via TLC with instant thin-layer chromatography paper (Gelman Sciences).

Cell Lines

The human MDA-MB-435S mammary carcinoma cell line (American Type Culture Collection, Manassas, Va.) was transfected with exon 9-deleted E-cadherin cDNA and wild-type E-cadherin cDNA, respectively (5). The cells were grown at 37° C. in a humidified atmosphere with 5% $CO_2$ in DMEM containing 4.5 g/l glucose supplemented with 10% FCS. For selection of the transfected MDA-MB-435S cells Geneticin was added to the cell medium. The cells were harvested by rinsing the monolayer with 1 mM EDTA and counted in a hemocytometer.

Determination of Antigen Density of Mutant E-Cadherin Transfected Cells and Binding Characteristics of the Labeled MAb The antigen density and binding characteristics of the radiolabeled MAb were analyzed by Scatchard analysis.

Mutant E-cadherin transfected cells ($10^6$) were incubated with increasing concentrations of d9MAbs labeled with $^{125}$I or $^{213}$Bi. Specific binding was confirmed by the failure of radiolabeled d9MAb to bind to cells expressing wild-type E-cadherin. Antigen density was also determined for unlabeled and chelate-coupled MAbs by indirect immunofluorescence with flow cytometry. The fluorescence signal was quantified by a calibration curve established with fluorescence quantitation beads (Quantibrite PE; Becton Dickinson).

Animal Models

To investigate the specific binding properties of $^{213}$Bi-labeled d9Mab, two different tumor models, a s.c. solid tumor model as well as an i.p. tumor model, were established. For that purpose, 4–5 week old female athymic mice were inoculated s.c. or i.p. with $1\times10^7$ cells expressing either mutant E-cadherin or wild-type E-cadherin as a negative control. After i.p. injection, two mice were sacrificed every 2 days until day 12 and thereafter at weekly intervals for histological examination of i.p. tumor progression. All experiments with mice were performed in accordance with the guidelines for the use of living animals in scientific studies and the "German Law for the Protection of Animals."

Biodistribution Studies

Mice, bearing s.c. tumors of 100–200 mg derived from both mutant and wild-type E-cadherin transfected cells (4–5 weeks after tumor cell inoculation), were injected i.v. with 3.7 MBq (100 $\mu$Ci) of $^{213}$Bi-d9Mab to study the accumulation in tumors and organs at 45 min and at 3 h postinjection. In addition, 37 kBq (1 $\mu$Ci) of the radioimmunoconjugate were injected directly into the tumor at three different sites. After injection, the tumors were removed, immediately frozen, cut into 8-$\mu$m sections, and analyzed for intratumoral distribution of the radioimmunoconjugate via exposure (15 min) to a high-sensitive Micro Imager system, which is capable of a spatial resolution of 10–15 $\mu$m (Biospace Measures, Paris, France).

Animals bearing small i.p. tumor nodules (0.1–2.0 mm in diameter) with or without ascites (~3–4 weeks after i.p. tumor cell inoculation) received an injection of 3 MBq (80 $\mu$Ci) of $^{213}$Bi-d9MAb into the peritoneal cavity and were sacrificed at 45 min and 3 h post injection. Tumor nodules and various normal tissues were removed, washed, and weighed, and the activity was determined by gamma counting using the 440-keV $\gamma$-emission of $^{213}$Bi. The results were expressed as a percentage of the injected dose/g of tissue ( % ID/g). Each reported value represents the mean and the SD of eight animals. Ascites volume was measured, and, after centrifugation, the activity in the pellet and the supernatant was determined.

To obtain scintigraphic images with optimal resolution (E$\gamma$ $^{111}$In, 172 and 249 keV; E$\gamma$ $^{213}$Bi, 440 keV) and to gain information about the long-term retention (t ½ $^{111}$In, 2.6 d; t ½ $^{213}$Bi, 46 min) of the immunoconjugate in mice bearing i.p. tumor nodules expressing either mutant or wild-type E-cadherin and in mice without tumor, scintigraphic images were taken at 3, 24, and 48 h after i.p. injection of $^{111}$In-labeled d9MAb (740 kBq). Immediately after the 48 h scintigram, the animals were sacrificed and the distribution of $^{111}$In immunoconjugate in representative organs was determined and expressed as % ID/g.

Statistical Analysis

Unpaired Student's t tests were performed to compare the mean values. Ps$\leq$0.05 were considered statistically significant.

Results

Antibody Specificity

Specific binding of the rat d9MAb reacting with mutant, but not with wild-type, E-cadherin was demonstrated by Western blot and immunohistochemistry. In human tissue, d9Mab reacted only with tumor cells of diffuse-type gastric cancer with an exon 9 deletion and did not show any cross-reaction to any normal human tissue similar to the clone 7E6, as described previously (6).

Radiolabeling and Tumor Cell Binding of d9MAb

The labeling efficiency of CHX-A0-DTPA-d9MAb with $^{213}$Bi was >90% at a specific activity of 1.48 GBq/mg (40 mCi/mg). The binding characteristics of $^{213}$Bi- and $^{125}$I-labeled d9MAb to MDA-MB-435S cellstransfected with mutant E-cadherin were evaluated by Scatchard analysis. With both $^{125}$I-labeled and $^{213}$Bi-conjugated MAbs, $5.5\times10^4$ binding sites/cell and a dissociation constant of 1.9 nmol/l were determined. These results were confirmed by flow cytometry using unconjugated and CHX-A0-DTPA-conjugated MAbs. The results demonstrated that conjugation and $^{213}$Bi-labeling of the MAb do not influence the binding characteristics. The binding of both radiolabeled MAbs to cells expressing wild-type E-cadherin was <4% compared with mutant E-cadherin-expressing cells.

Development of the Tumor Models s.c. tumors of 100–200 mg in weight developed 4–5 weeks after s.c. inoculation of $1\times10^7$ tumor cells. Up to day 6 after i.p. inoculation of mutant and wild-type E-cadherin-transfected cells, single tumor cells and small tumor-cell clusters consisting of ~100 cells could be detected histologically in the peritoneal cavity. After day 10, tumor attachment to the visceral organs and the peritoneum could be demonstrated microscopically. Beginning from day 20 after tumor cell inoculation, macroscopic tumor nodules in the mesenterium ranging from 0.1 to 2 mm in diameter could be observed (FIG. 7a). Histological sections from these tumor nodules showed tumor cells on the serosa and also invasive tumor cells with a desmoplastic reaction (FIG. 7b). The tumor cells on the serosa often lost their cell-to-cell contact, and isolated tumor cells or cell clusters could be detected in the ascites. Forty percent of the animals developed ascites that contained up to $1\times10^8$ tumor cells/ml as single cells and as cell clusters (FIG. 7c). At this stage of tumor development, the animals were used for biodistribution studies after i.p. injection of the $^{213}$Bi immunoconjugate.

Biodistribution Studies of $^{213}$Bi- and $^{111}$In-d9MAb

In the s.c. tumor model, the activity concentration of $^{213}$Bi-d9MAb 3 h after i.v. injection was lower than in the blood; this was as expected for intact MAbs, which slowly diffuse from the circulation into solid tumor tissue. However, binding in tumors expressing mutant E-cadherin was 3-fold higher than in tumors expressing wild-type E-cadherin. After intratumoral injection in s.c. tumors, the specific binding of $^{213}$Bi-d9MAb to mutant E-cadherin could be demonstrated by auto-radiographic images. FIG. 8a shows local retention of the $^{213}$Bi immunoconjugate at the three injection sites in the center of the tumor that expressed E-cadherin with an exon 9 deletion. Retention is also seen at the three puncture sites on the tumor periphery. In contrast, tumors expressing wild-type E-cadherin did not show any specific retention of the $^{213}$Bi coupled MAb (FIG. 8b). In the i.p. tumor model, $^{213}$Bi-d9MAb was injected into the peritoneal cavity 3–4 weeks after the inoculation of tumor cells expressing mutant E-cadherin or wild-type E-cadherin, and the biodistribution was quantified at 45 min and 3 h postinjection. The results are summarized in Table 6. In animals that had not developed ascites, a high specific uptake of up to 62±14% ID/g at 45 min and 58±19% ID/g at 3 h was observed in small tumor nodules expressing mutant E-cadherin. In the wild-type E-cadherin model, uptake was only 3.7±1.0% ID/g at 45 min and 3.4±0.9 at 3 h. In all other tissues, the uptake of $^{213}$Bi immunoconjugate was low. The low $^{213}$Bi accumulation in the kidneys, which are known to accumulate free bismuth, indicates the stability of the immunoconjugate. In animals bearing tumors expressing wild-type E-cadherin that does not bind the MAb, however, uptake in normal tissue was statistically significantly higher than in animals expressing mutant E-cadherin. In mice with ascites (up to 5 ml), the concentration of $^{213}$Bi -d9MAb in tumor nodules and the other organs was statistically significantly reduced compared with animals without ascites, depending on the volume of ascites and the number of tumor cells in the fluid. This result suggests that the antibody was rapidly and firmly bound to free accessible mutant E-cadherin on tumor cells in the ascites. After centrifugation of ascites with cells expressing mutant E-cadherin, 78% of the $^{213}$Bi activity was recovered in the cell pellet in contrast with 18% bound in the pellet of ascites from cells expressing wild-type E-cadherin. Scintigraphic images of mice bearing small tumor nodules, expressing mutant E-cadherin or wild-type E-cadherin, and of mice without tumor obtained 48 h after i.p. injection of $^{111}$In-d9Mab, are shown in FIG. 9. In mice without tumor, the activity is mainly distributed in the blood pool of heart, lungs, and liver (FIG. 9a). A similar activity distribution was found for mice bearing tumors that expressed wild-type E-cadherin (FIG. 9c). This indicates that in both cases most of the activity was reabsorbed from the peritoneal cavity. Conversely, in the mouse with multiple i.p. tumor nodules expressing mutant E-cadherin, a considerable amount of activity was retained in the peritoneal cavity, resulting in a clearly visible lower background activity compared with the two controls (FIG. 9b). Tissue distribution data of $^{111}$In were in accordance with the results of the scintigraphic images. Activity accumulation in tumor nodules expressing mutant E-cadherin, was 56% ID/g compared with 4.8% ID/g in controls. Activity concentration of $^{111}$In in the blood of animals inoculated with wild-type E-cadherin-expressing cells and of animals without tumor cell inoculation was 11% ID/g compared with 5% ID/g in animals with tumor nodules expressing mutant E-cadherin.

Discussion

Early i.p. dissemination of tumor cells is a crucial event in the course of gastric carcinoma, resulting in peritoneal carcinomatosis and rapid deterioration of the patient's clinical status. Apart from a few experimental therapeutic strategies, there is currently no specific treatment for peritoneal cancer spread. Effective treatment of the i.p. compartment would require locoregional administration of a cytotoxic substance into the peritoneal cavity that could specifically bind to diffusely spread tumor cells and cell clusters. Monoclonal antibodies that specifically recognize tumor cell antigens coupled with a radionuclide with high LET are promising candidates. Because the d9MAb used in the present experiments specifically binds to mutant E-cadherin expressed by diffuse-type gastric carcinoma, it is an ideal vehicle to attach radionuclides to gastric carcinoma cells that have spread diffusely into the peritoneal cavity. By choosing the appropriate radionuclide, the range of the cytotoxic effect can be matched to the size of the tumor. For the radioimmunotherapy of malignancies with large tumor masses, β-emitting radionuclides such as $^{131}$I, $^{188}$Re, or $^{90}$Y, with mean tissue ranges of 0.9 to 3.9 mm, have been coupled to MAbs. For selective irradiation of single tumor cells or small tumor cell clusters, the new approach of labeling tumor-specific MAbs with α-emitting nuclides seems to be very promising. The α-particles emitted by $^{212}$Bi, $^{211}$At, and $^{213}$Bi have short ranges of only 50–100 μm and a high LET of ~100 keV/μm that deposit a large amount of energy within a few cell diameters. α-Emitter immunoconjugates have proven to be powerful therapeutic agents in animal experiments (11–13), especially for malignancies that spread on the surface of the body cavities, such as ovarian cancer and malignant meningitis (14–16).

Herein, a nude mouse model was developed for i.p. tumor spread similar to that which occurs in patients with diffuse-type gastric cancer. In this model, d9MAb demonstrated high and specific binding to small tumor nodules established from tumor cells expressing mutant E-cadherin, whereas binding of d9MAb to tumors expressing wild-type E-cadherin was comparatively low. In addition, the $^{213}$Bi -labeled d9MAb bound to the tumor cells in the i.p. cavity within less than one half-life of $^{213}$Bi (46 min). The binding remained stable at least 3 h after injection, when 94% of the injected $^{213}$Bi activity had decayed at the tumor site. The number of antigen molecules on the E-cadherin-transfected tumor cells was calculated to be $5.5 \times 10^4$ cell by Scatchard analysis. At a specific activity of 1.48 GBq/mg, $^{213}$Bi-labeled d9MAb can attach 40 α-particles to a tumor cell. It has been reported in a number of cell lines that 3–9 α-particles bound/cell can reduce clonogenic cell survival to as low as 10% (17–19). Because the antigen density on human diffuse gastric carcinoma cells as shown by immunohistochemistry may exceed that of our tumor model, binding of $^{213}$Bi immunoconjugates should be sufficient to guarantee destruction of almost all of the tumor cells. By increasing the specific activity without the loss of immunoreactivity caused by radiolysis, the specificity of binding and the therapeutic efficiency could probably be improved further.

The beneficial therapeutic effects of α-emitter-immunoconjugates are currently being evaluated in two clinical trials. Patients suffering from acute myeloic leukemia are being treated with $^{213}$Bi-labeled HuM195 MAb recognizing CD33, a differentiation antigen expressed in leukemic cells. More than one-half of the 17 patients treated thus far have shown a reduction of leukemic cells in the peripheral blood, and a few also have shown decreased numbers of bone marrow blast cells (20). The MAb 81C6 specifically binds to the matrix glycoprotein tenascin that is expressed by glioma cells but not by normal brain tissue. The $^{211}$At labeled antibody has been applied locally to the surgical cavity created by the glioma resection with promising results (16). The results obtained in our experimental model with the d9Mab labeled with $^{213}$Bi suggest that this radioimmunoconjugate and similar ones targeting other E-cadherin mutations (e.g., exon 8 deletion) should be tested in clinical therapeutic trials for a subgroup of diffuse-type gastric carcinoma patients. This would be the first application of such a method in disseminated gastro-intestinal tumors.

TABLE 6

Biodistribution of $^{213}$Bi d9MAb in animals with i.p. tumors expressing mutant or wild-type E-cadherin, 45 min and 3 h after i.p. injection:

| organ | Mutant E-cadherin without ascites | | Mutant E-caderin with ascites | | Wild-type E-cadherin without ascites | |
|---|---|---|---|---|---|---|
| | 45 min | 3 h | 45 min | 3 h | 45 min | 3 h |
| Blood | 1.1 ± 0.4 | 2.6 ± 0.9 | 0.4 ± 0.1 | 1.4 ± 0.4 | 2.8 ± 0.6 | 5.9 ± 1.4 |
| Tumor | 62 ± 14 | 58 ± 19 | 7.1 ± 3.4 | 9.3 ± 4.2 | 3.7 ± 1.0 | 3.4 ± 0.9 |
| Heart | 0.5 ± 0.1 | 1.1 ± 0.3 | 0.1 ± 0.03 | 0.5 ± 0.1 | 1.5 ± 0.4 | 2.1 ± 0.3 |
| Lung | 0.7 ± 0.2 | 1.4 ± 0.4 | 0.2 ± 0.08 | 0.6 ± 0.2 | 1.1 ± 0.3 | 2.0 ± 0.6 |
| Spleen | 1.0 ± 0.4 | 1.2 ± 0.5 | 0.3 ± 0.07 | 0.9 ± 0.2 | 1.6 ± 0.4 | 1.9 ± 0.8 |
| Stomach | 2.1 ± 1.0 | 1.7 ± 0.4 | 0.6 ± 0.1 | 0.8 ± 0.3 | 3.3 ± 0.9 | 4.1 ± 1.3 |
| Bowel | 1.4 ± 0.3 | 1.2 ± 0.3 | 0.8 ± 0.3 | 0.9 ± 0.3 | 2.8 ± 0.6 | 2.9 ± 0.7 |
| Peritoneum | 3.9 ± 1.8 | 3.2 ± 1.4 | 2.5 ± 0.9 | 3.1 ± 1.2 | 2.3 ± 0.1 | 1.8 ± 0.3 |
| Kidney | 3.6 ± 1.4 | 5.1 ± 1.9 | 2.8 ± 1.2 | 4.0 ± 0.8 | 4.1 ± 1.3 | 6.8 ± 2.3 |
| Liver | 1.2 ± 0.4 | 2.1 ± 0.8 | 0.5 ± 0.1 | 1.2 ± 0.4 | 2.5 ± 0.3 | 3.8 ± 0.9 |
| Muscle | 0.1 ± 0.08 | 0.4 ± 0.1 | 0.09 ± 0.03 | 0.2 ± 0.06 | 0.4 ± 0.1 | 0.6 ± 0.1 |
| Ascites | | | 14.4 ± 6.3 | 17.3 ± 5.6 | | |

References

1. Wikstrand C. J., McLendon, R. E., Friedman, A. H., and Bigner D. D. Cell surface localization and density of the tumor-associated variant of the epidermal growth factor receptor, EGFRVIII. Cancer Res., 57: 4130–4140, 1997.
2. Reist, C. J., Archer, G. E., Wikstrand, C. J., Bigner, D. D., and Zalutsky, M. R. Improved targeting of an anti-epidermal growth factor receptor variant III monoclonal antibody in tumor xenografts after labeling using N-Succinimidyl 5-iodo-3-pyridin-ecarboxylate. Cancer Res., 57: 1510–1515, 1997.
3. Reist, C. J., Foulon, C. F., Alston, K., Bigner, D. D., and Zalutsky, M. R. Astatine-211 labeling of internalizing anti-EGFRvIII monoclonal antibody using N-Succinimidyl 5-[211 At]Astato-3-pyridinecarboxylate. Nucl. Med. Biol., 26: 405–411, 1999.
4. Becker, K-F., Atkinson, M. J., Reich, U., Becker, I., Nekarda, H., Siewert, J. R., and HÖfler, H. E-cadherin gene mutations provide clues to diffuse type gastric carcino-mas. Cancer Res., 54: 3845–3852, 1994.
5. Handschuh, G., Candidus, S., Luber, B., Reich, U., Schott, C., Oswald, S., Becke, H., Hutzler, P., Birchmeier, W., H öfler, H., and Becker, K-F. Tumor-associated E-cadherin mutations alter cellular morphology, decrease cellular adhesion, and increase cellular motility. Oncogene, 18: 4301–4312, 1999.
6. Becker, K-F., Kremmer, E., Eulitz, M., Becker, I., Handschuh, G., Schuhmacher, C., Müller, W., Gabbert, H. E., Ochiai, A., Hirohashi, S., and Höfler, H. Analysis of E-cadherin in diffuse-type gastric cancer using a mutation-specific monoclonal antibody. Am. J. Pathol., 155: 1803–1809, 1999.
7. Brechbiel, M. W., Pippin, C. G., McMurry, T. J., Milenic, D., Roselli, M., Colcher, D., Gansow, O. A. An effective chelating agent for labeling of monoclonal antibody with Bi-212 for a-particle mediated radioimmuno-therapy. J. Chem. Soc. Chem. Commun., 1169–1170: 1991.
8. Nikula, T. K., McDevitt, M. R., Finn, R. D., Wu, C., Kozak, R. W., Garmestani, K., Brechbiel, M. W., Curcio, M. J., Pippin, C. G., Tiffany-Jones, L., Geerlings, M. W., Sr., Apostolidis, C., Molinet, R., Geerlings, M. W., Jr., Gansow, O. A., Scheinberg, D. A. a-Emitting bismuth cyclohexylbenzyl DTPA constructs of recombinant humanized anti-CD33 antibodies: pharmacokinetics, bioactivity, toxicity, and chemistry. J. Nucl. Med., 40: 166–176, 1999.
9. Nikula, T. K., Curcio, M. J., Brechbiel, M. W., Gansow, O. A., Finn, R. D., Scheinberg, D. A. A rapid, single vessel method for preparation of clinical grade ligand conjugated monoclonal antibodies. Nucl. Med. Biol., 22: 387–390, 1995.
10. Koch, L., Apostolidis, C., Janssens, W., Molinet, R., van Geel, J. Production of Ac-225 and application of the Bi-213 daughter in cancer therapy. Czech. J. Phys., 40: 817–822, 1999.
11. Huneke, R. B., Pippin, C. G., Squire, R. A., Brechbiel, M. W., Gansow, O. A., and Strand, M. Effective a-particle-mediated radioimmunotherapy of murine leukemia. Cancer Res., 52: 5818–5820, 1992.
12. Béhé, T. M., M., Stabin, M. G., Wehrmann, E., Apostolidis, C., Molinet, R., Strutz, F., Fayyazi, A., Wieland, E., Gratz, S., Koch, L., Goldenberg, D. M., and Becker, W. High-linear Energy Transfer (LET) a versus Low-LET β emitters in radioimmunotherapy of solid tumors: therapeutic efficacy and dose-limiting toxicity of 213 Bi-versus 90 Y-labeled CO17-1A Fab9 fragments in a human colonic cancermodel. Cancer Res., 59: 2635–2643, 1999.
13. Kennel S. J., Stabin, M., Yoriyaz, H., Brechbiehl, M., and Mirzadeh, S. Treatment of lung tumor colonies with 90 Y targeted to blood vessels: comparison with the a-particle emitter $^{213}$Bi. Nucl. Med. Biol., 26: 149–157, 1999.
14. Vergote, I., Larsen, R. H., de Vos, L., Winderen, M., Ellingsen, T., Bjørgum, J., Hoff, P., Aas, M., Tropé, C., and Nustad, K. Distribution of intraperitoneally injected microsheres labeled with the a-emitter astatine ($^{211}$At) compared with Phosphorus (32 P) and yttrium (90 Y) colloids in mice. Gynecol. Oncol., 47: 358–365, 1992.
15. Andersson, H., Lindegren, S., Back, T., Jacobsson, L., Leser, G., and Horvath, G. Radioimmunotherapy of nude mice with intraperitoneally growing ovarian cancer xenograft utilizing 211 At-labeled monoclonal antibody MOv18. Anticancer Res., 20: 459–462, 2000.
16. Zalutsky, M. R., Vaidyanathan, G. Astatine-211-labeled radiotherapeutics: an emerg-ing approach to targeted a-particle radiotherapy. Curr. Pharm. Des., 6: 1433–1455, 2000.

17. Humm, J. L., Roeske, J. C., Fisher, D. R., and Chen, G. T. Y. Microdosimetric concepts in radioimmunotherapy. Med. Phys., 20: 535–541, 1993.
18. Roeske, J. C., and Stinchcomb, T. G. Dosimetric framework for therapeutic a-particle emitters. J. Nucl. Med., 38: 1923–1929, 1997.
19. Larsen, R. H., Akabani, G., Welsh, P., and Zalutsky, M. R. The cytotoxicity and microdosimetry of Astatine-211-labeled chimeric monoclonal antibodies in human glioma and melanoma cells in vitro. Radiat. Res., 149: 155–162, 1998.
20. McDevitt, M. R., Sgouros, G., Finn, R. D., Humm, J. L., Jurcic, J. G., Larson, S. M., and Scheinberg, D. A. Radioimmunotherapy with α-emitting nuclides. Eur. J. Nucl. Med., 25: 1341–1351, 1998.

We claim:

1. A method for treating diffuse gastric carcinoma in an animal, wherein the diffuse gastric carcinoma cells express a mutated E-cadherin comprising SEQ ID NO:2, 4, 6, 8, 10, 12, 14, 16, 18 or 20, the method comprising:
   administering to the animal an immunoconjugate comprising a monoclonal antibody which recognizes SEQ ID NO:2, 4, 6, 8, 10, 12, 14, 16, 18 or 20 wherein the immunoconjugate is in a dosage effective to substantially eliminate the diffuse gastric carcinoma in said animal.

2. A method of treating diffuse gastric carcinoma in an animal, comprising:
   a) determining the absence or presence of a diffuse gastric cancer which expresses any one of the mutated E-cadherin sequences of SEQ ID NO:2, 4, 6, 8, 10, 12, 14, 16, 18 or 20, by:
      i. providing at least one monoclonal antibody that recognizes SEQ ID NO:2, 4, 6, 8, 10, 12, 14, 16, 18 or 20,
      ii. contacting said at least one monoclonal antibody with cells or tissues suspected to be diffuse gastric cancer cells or tissues, and
      iii. determining the amount of said at least one monoclonal antibody bound to said cells or tissues, and in case of presence b) treating the animal in accordance with the method of claim 1.

3. The method of any of claim 1 or claim 2, wherein the animal is a mammal.

4. The method of claim 3, wherein the mammal is a human.

5. The method of claim 1, wherein the monoclonal antibody is 7E6 (secreted by the hybridona having the accession number DSM ACC2277).

6. The method of claim 1, wherein the immunoconjugate comprising a radionuclide or a toxin.

7. The method of claim 6, wherein the radionuclide is $^{131}$I, $^{188}$Re, $^{90}$Y, $^{212}$Bi, $^{211}$At, or $^{213}$Bi.

8. The method of claim 6, wherein the toxin is Pseudomanas exotoxin, Ricin, DMl, or Doxorubicin.

* * * * *